US011510659B2

(12) United States Patent
Berthier et al.

(10) Patent No.: US 11,510,659 B2
(45) Date of Patent: Nov. 29, 2022

(54) BODILY FLUID COLLECTION DEVICES AND RELATED METHODS

(71) Applicant: Tasso, Inc., Seattle, WA (US)

(72) Inventors: Erwin Berthier, Seattle, WA (US); Ben Casavant, Seattle, WA (US); Jake Myre, Seattle, WA (US)

(73) Assignee: Tasso, Inc., Seattle, WA (US)

( * ) Notice: Subject to any disclaimer, the term of this patent is extended or adjusted under 35 U.S.C. 154(b) by 0 days.

(21) Appl. No.: 17/186,369

(22) Filed: Feb. 26, 2021

(65) Prior Publication Data

US 2021/0196245 A1 Jul. 1, 2021

Related U.S. Application Data

(63) Continuation of application No. 16/571,028, filed on Sep. 13, 2019.
(Continued)

(51) Int. Cl.
*A61B 10/00* (2006.01)
*A61B 5/15* (2006.01)
*A61B 5/151* (2006.01)

(52) U.S. Cl.
CPC ........ *A61B 10/0045* (2013.01); *A61B 5/1405* (2013.01); *A61B 5/150053* (2013.01);
(Continued)

(58) Field of Classification Search
CPC .............. A61B 10/0045; A61B 5/1405; A61B 5/150053; A61B 5/150061;
(Continued)

(56) References Cited

U.S. PATENT DOCUMENTS

| 4,653,513 A | 3/1987 | Dombrowski |
| 4,660,570 A | 4/1987 | Dombrowski |

(Continued)

FOREIGN PATENT DOCUMENTS

| CN | 1917810 A | 2/2007 |
| CN | 102309331 | 4/2013 |

(Continued)

OTHER PUBLICATIONS

Javier Atemcoa and David J. Beebe, "Controlled Microfluidic Interfaces," Sep. 29, 2005, pp. 648-655, vol. 437, No. 7059, Publisher: Nature.
(Continued)

*Primary Examiner* — Devin B Henson
(74) *Attorney, Agent, or Firm* — Perkins Coie LLP

(57) ABSTRACT

Devices and methods for withdrawing bodily fluid from a patient are disclosed herein. A handheld device configured in accordance with the present technology can include a housing having an opening, a skin-piercing assembly located at least partially within the housing, and an actuator movable relative to the housing along a deployment direction. The skin-piercing assembly can include a skin-piercing feature and a biasing member. The biasing member can be coupled to the skin-piercing feature to bias the skin-piercing feature along the deployment direction. Movement of the actuator along the deployment direction to a predetermined position can increase a load on the biasing member to at least a partially loaded state. Movement of the actuator along the deployment direction beyond the predetermined position can release the load on the biasing member so that the biasing member actively drives the skin-piercing feature along the deployment direction.

22 Claims, 28 Drawing Sheets

Related U.S. Application Data

(60) Provisional application No. 62/731,728, filed on Sep. 14, 2018.

(52) U.S. Cl.
CPC .. *A61B 5/150061* (2013.01); *A61B 5/150099* (2013.01); *A61B 5/15117* (2013.01); *A61B 5/150221* (2013.01); *A61B 5/150374* (2013.01)

(58) Field of Classification Search
CPC ........ A61B 5/150099; A61B 5/150221; A61B 5/15117; A61B 5/150022; A61B 5/15113; A61B 5/15194; A61B 5/150343; A61B 5/15144; A61B 5/15111
See application file for complete search history.

(56) References Cited

U.S. PATENT DOCUMENTS

| | | | |
|---|---|---|---|
| 4,775,336 A | 10/1988 | Paulo | |
| 4,775,366 A | 10/1988 | Rosenblatt | |
| 5,035,865 A | 7/1991 | Inaba et al. | |
| 5,145,565 A | 9/1992 | Kater et al. | |
| 5,318,584 A | 6/1994 | Lange et al. | |
| 5,320,607 A | 6/1994 | Ishibashi | |
| 5,356,420 A | 10/1994 | Czernecki et al. | |
| 5,569,287 A * | 10/1996 | Tezuka | A61B 5/150022 606/182 |
| 5,611,809 A | 3/1997 | Marshall et al. | |
| 5,636,640 A | 6/1997 | Staehlin | |
| 5,772,677 A | 6/1998 | Mawhirt et al. | |
| 6,010,519 A | 1/2000 | Mawhirt et al. | |
| 6,042,595 A | 3/2000 | Morita | |
| 6,152,942 A | 11/2000 | Brenneman et al. | |
| 6,221,089 B1 | 4/2001 | Mawhirt | |
| 6,226,378 B1 | 5/2001 | Quattrocchi | |
| 6,364,890 B1 | 4/2002 | Lum et al. | |
| 6,419,661 B1 | 7/2002 | Kuhr et al. | |
| 6,432,120 B1 | 8/2002 | Teo | |
| 6,605,048 B1 | 8/2003 | Levin et al. | |
| 6,659,975 B2 | 12/2003 | Amano et al. | |
| 6,660,018 B2 | 12/2003 | Lum et al. | |
| 6,706,000 B2 | 3/2004 | Perez et al. | |
| 6,821,485 B2 | 11/2004 | Beebe et al. | |
| 6,849,052 B2 | 2/2005 | Uchigaki | |
| 6,856,821 B2 | 2/2005 | Johnson | |
| 6,929,650 B2 * | 8/2005 | Fukuzawa | A61B 5/15186 600/576 |
| 7,160,313 B2 | 1/2007 | Galloway et al. | |
| 7,316,698 B1 | 1/2008 | Galloway et al. | |
| 7,344,499 B1 | 3/2008 | Prausnitz et al. | |
| 7,374,545 B2 | 5/2008 | Alroy et al. | |
| 7,452,365 B2 | 11/2008 | Galloway et al. | |
| 7,666,149 B2 | 2/2010 | Simons et al. | |
| 7,670,300 B2 | 3/2010 | Vreeke et al. | |
| 7,704,265 B2 | 4/2010 | Schraga | |
| 7,775,991 B2 * | 8/2010 | Feaster | A61B 5/150519 600/584 |
| 7,803,123 B2 | 9/2010 | Perez et al. | |
| 7,846,110 B2 | 12/2010 | Kloepfer et al. | |
| 7,879,058 B2 | 2/2011 | Ikeda | |
| 7,981,131 B2 | 7/2011 | Shi | |
| 7,998,161 B2 | 8/2011 | Shi | |
| 8,025,628 B2 | 9/2011 | Wong et al. | |
| 8,034,628 B2 | 10/2011 | Harrison et al. | |
| 8,382,681 B2 | 2/2013 | Escutia et al. | |
| 8,454,642 B2 | 6/2013 | Schraga | |
| 8,512,367 B2 | 8/2013 | Robbins et al. | |
| 8,551,047 B2 | 10/2013 | Burns et al. | |
| 8,696,596 B2 | 4/2014 | Douglas et al. | |
| 8,715,307 B2 | 5/2014 | Sun | |
| 8,728,411 B2 | 5/2014 | Beebe et al. | |
| 8,821,412 B2 | 9/2014 | Gonzalez-Zugasti et al. | |
| 8,840,634 B2 | 9/2014 | Sun et al. | |
| 8,876,846 B2 | 11/2014 | Schraga | |
| 9,033,898 B2 | 5/2015 | Chickering, III et al. | |
| 9,138,184 B2 | 9/2015 | Lum | |
| 9,220,447 B2 | 12/2015 | Richter et al. | |
| 9,289,763 B2 | 3/2016 | Berthier et al. | |
| 9,724,031 B2 | 8/2017 | Yi et al. | |
| 9,839,384 B2 | 12/2017 | Escutia et al. | |
| 9,987,629 B2 | 6/2018 | Berthier et al. | |
| 10,034,627 B2 | 7/2018 | Booker et al. | |
| 10,105,080 B1 | 10/2018 | Kam et al. | |
| 10,426,390 B2 | 10/2019 | Berthier et al. | |
| 10,492,716 B2 | 12/2019 | Berthier et al. | |
| 10,765,361 B2 * | 9/2020 | Krasnow | A61B 5/150236 |
| 10,779,757 B2 | 9/2020 | Berthier et al. | |
| 11,033,212 B2 | 6/2021 | Berthier et al. | |
| 11,395,614 B2 | 7/2022 | Berthier et al. | |
| 2002/0055711 A1 | 5/2002 | Lavi et al. | |
| 2002/0097632 A1 | 7/2002 | Kellogg et al. | |
| 2003/0018282 A1 | 1/2003 | Effenhauser et al. | |
| 2003/0028125 A1 | 2/2003 | Yuzhakov et al. | |
| 2003/0216767 A1 | 11/2003 | List et al. | |
| 2003/0225362 A1 | 12/2003 | Currie et al. | |
| 2004/0092996 A1 | 5/2004 | List et al. | |
| 2004/0176704 A1 | 9/2004 | Stevens et al. | |
| 2004/0243105 A1 | 12/2004 | Swan et al. | |
| 2005/0236566 A1 | 10/2005 | Liu | |
| 2006/0052809 A1 | 3/2006 | Karbowniczek et al. | |
| 2006/0171855 A1 | 8/2006 | Yin et al. | |
| 2007/0010841 A1 | 1/2007 | Teo et al. | |
| 2007/0161106 A1 | 7/2007 | Jervis et al. | |
| 2007/0212266 A1 | 9/2007 | Johnston et al. | |
| 2007/0213638 A1 | 9/2007 | Herbrechtsmeier et al. | |
| 2007/0260193 A1 | 11/2007 | Chin et al. | |
| 2008/0028821 A1 | 2/2008 | Horkiike et al. | |
| 2008/0097502 A1 | 4/2008 | Winters-Hilt et al. | |
| 2009/0036915 A1 | 2/2009 | Karbowniczek et al. | |
| 2009/0118753 A1 | 5/2009 | Dicesare et al. | |
| 2009/0187118 A1 | 7/2009 | Kim et al. | |
| 2009/0192486 A1 | 7/2009 | Wilmot et al. | |
| 2010/0023045 A1 | 1/2010 | Macho et al. | |
| 2010/0145377 A1 | 6/2010 | Lai et al. | |
| 2010/0256465 A1 | 10/2010 | Bernstein et al. | |
| 2010/0256524 A1 | 10/2010 | Levinson et al. | |
| 2010/0326826 A1 | 12/2010 | Harrison et al. | |
| 2011/0029006 A1 | 2/2011 | Leong | |
| 2011/0077553 A1 | 3/2011 | Alroy | |
| 2011/0087134 A1 | 4/2011 | Lathrop et al. | |
| 2011/0165022 A1 | 7/2011 | Meathrel et al. | |
| 2011/0306853 A1 | 12/2011 | Black et al. | |
| 2011/0312773 A1 | 12/2011 | Silbebrook et al. | |
| 2012/0048391 A1 | 3/2012 | Delamarche et al. | |
| 2012/0048931 A1 | 3/2012 | Delamarche et al. | |
| 2012/0088249 A1 | 4/2012 | Jovanovich et al. | |
| 2013/0211289 A1 | 8/2013 | Moga et al. | |
| 2014/0042094 A1 | 2/2014 | Montagu et al. | |
| 2014/0190894 A1 | 7/2014 | Beebe et al. | |
| 2014/0273056 A1 | 9/2014 | Beebe et al. | |
| 2015/0238705 A1 | 8/2015 | Gravesen et al. | |
| 2015/0342509 A1 | 12/2015 | Peeters et al. | |
| 2016/0051981 A1 | 2/2016 | Berthier et al. | |
| 2016/0081606 A1 | 3/2016 | Russ et al. | |
| 2016/0256106 A1 | 9/2016 | Krasnow et al. | |
| 2017/0172481 A1 * | 6/2017 | Berthier | A61B 5/150022 |
| 2018/0008183 A1 | 1/2018 | Chickering, III et al. | |
| 2018/0078241 A1 | 3/2018 | Moga et al. | |
| 2018/0228418 A1 | 8/2018 | Berthier et al. | |
| 2019/0015827 A1 | 1/2019 | Berthier et al. | |
| 2020/0037940 A1 | 2/2020 | Berthier et al. | |
| 2020/0085414 A1 | 3/2020 | Berthier et al. | |
| 2020/0146606 A1 | 5/2020 | Casavant et al. | |
| 2020/0178870 A1 | 6/2020 | Berthier et al. | |
| 2020/0323473 A1 | 10/2020 | Berthier et al. | |
| 2022/0039710 A1 | 2/2022 | Berthier et al. | |

FOREIGN PATENT DOCUMENTS

| | | |
|---|---|---|
| CN | 103370007 | 10/2013 |
| EP | 1389443 | 2/2004 |
| EP | 1808128 | 7/2007 |
| EP | 2439540 | 4/2012 |

(56) References Cited

FOREIGN PATENT DOCUMENTS

| EP | 2484448 | 8/2012 |
|---|---|---|
| EP | 2863798 | 4/2015 |
| EP | 3725226 A1 | 10/2020 |
| WO | WO2002100253 | 12/2002 |
| WO | WO208053743 | 5/2008 |
| WO | WO2013112877 | 8/2013 |
| WO | WO2017112793 | 6/2017 |
| WO | WO2018022535 | 2/2018 |
| WO | WO2018057760 | 3/2018 |
| WO | WO2019114343 | 6/2019 |
| WO | WO2014018558 | 1/2020 |
| WO | WO2020056382 | 3/2020 |
| WO | WO2020102281 | 5/2020 |
| WO | WO2020223710 | 11/2020 |
| WO | WO2021041881 | 3/2021 |

OTHER PUBLICATIONS

Scott M. Berry, Elaine T. Alarid, and David J. Beebe, "One-step purification of nucleic acid for gene expression analysis via Immiscible Filtration Assisted by Surface Tension (IFAST)," May 21, 2011, pp. 1747-1753, vol. 11, No. 10, Publisher: Lab Chip.

David Chunningham, Timothy Henning, Eric Shain, Douglas Young Jurgen Hanning, Eric Barua, and Raphael Lee, "Blood extraction from lancet wounds using vacuum combined with skin stieLching," Nov. 9, 2001, pp. 1089-1096, vol. 92, No. 3, Publisher: J Appl Physiol.

H Fruhstorfer, H Lange, "Capillary blood sampling: how much pain is necessary? Part 3: Pricking the finger can be less painful," Feb. 1, 1995, pp. 253-254, vol. 12, No. 6, Publisher: Practical Diabetes International.

H Fruhstorfer and T Muller, "Capillary blood sampling: how much pain is necessary? Part 1: Comparison of existing finger stick devices," Feb. 1, 1995, pp. 72-74, vol. 12, No. 2, Publisher: Practical Diabetes International.

H Fruhstorfer, T Muller, and E Scheer, "Capillary blood sampling: how much pain is necessary? Part 2: Relation between penetration depth and puncture pain," Feb. 1, 1995, pp. 184-185, vol. 12, No. 4, Publisher: Practical Diabetes International.

Heinrich Fruhstorfer, Gunther Schmelzeisen-Redeker, and Thomas Weiss, "Capillary Blood Sampling: relation between lancet diameter, lancing pain and blood volume," 1999, pp. 283-286, vol. 3, No. 3, Publisher: European Journal of Pain.

H Fruhstorfer, K Selzer, and O Selbman, "Capillary blood sampling: how much pain is necessary? Part 4: Comparison of lancets for automatic lancing devices," Jul. 24, 1995, pp. 58-60, vol. 13, No. 2, Publisher: Practical Diabetes International.

Heinrich Fruhstorfer, "Capillary Blood Sampling: the pain of single-use lancing devices," 2000, pp. 301-305, vol. 4, No. 3, Publisher: European Journal of Pain.

Chia-Hsien Hsu, Chihchen Chen, and Albert Folch, "Microcanals for micropipette access to single cells in microfluidic environments," Jul. 23, 2004, pp. 420-424, vol. 4, No. 5, Publisher: Lab Chip.

J. Berthier, F. Loe-Mie, V.-M. Tran, S Schoumacker, F. Mittler, G. Marchand, N. Sarrut, "On the Pinning of Interfaces on Micropillar Edges," Jun. 3, 2009, pp. 296-303, vol. 338, No. 1, Publisher: J Colloid Interface Sci.

Sung Hoon Lee, Austen James Heinz, Sunghwan Shin, Young-Gyun Jung, Sung-Eun Choi, Wook Park, Jung-Hye Roe, Sunghoon Kwon, "Capillary Based Patterning of Cellular Communities in the Laterally Open Channels," Apr. 1, 2010, pp. 2900-2906, vol. 82, No. 7, Publisher: Anal Chem.

"Open Microfluidic and Nanofluidic systems," Feb. 15, 2005, pp. 1848-1852, vol. 102, Publisher: PNAS.

Nuno M. Oliveira, Ana I. Neto, Wenlong Song, and Joao F. Mano, "Two-Dimensional Open Microfluidic Devices by Tuning the Wettability on Patterned Superhydrophobic Polymeric Surface," Aug. 6, 2010, vol. 3:085205, Publisher: Appl Phys Express.

Jessica Olofsson, Johan Pihl, Jon Sinclair, Eskil Sahlin, Mattias Karlsson, and Owe Orwar, "A Microfluidics Approach to the Problem of Creating Separate Solution Environments Accessible from Macroscopic Volumes", Sep. 1, 2004, pp. 4968-4976, vol. 76, No. 17, Publisher: Anal Chem.

Ralf Seemann, Martin Brinkmann, Edward J. Kramer, Frederick F. Lange, and Reinhard Lipowsky, "Wetting morphologies at microstructured surfaces," Dec. 16, 2004, pp. 1848-1852, vol. 102, No. 6, Publisher: Proc Natl Acad Sci USA.

Bin Zhao, Jeffrey S. Moore, and David J. Beebe, "Surface-Directed Liquid Flow Inside Microchannels," Feb. 9, 2001, pp. 1023-1026, vol. 291, No. 5506, Publisher: Science.

International Search Report and Written Opinion received for PCT Application No. PCT/US13/51731; Applicant: Erwin Berthier, dated Jan. 2, 2014, 16 pages.

International Search Report and Written Opinion received for PCT Application No. PCT/US16/68077; Applicant: Tasso, Inc., dated Mar. 10, 2017, 16 pages.

International Search Report and Written Opinion received for PCT Application No. PCT/US19/51186; Applicant: Tasso, Inc., dated Nov. 26, 2019, 12 pages.

Australian First Patent Examination Report received for Patent Application No. 2013293078; Applicant: Tasso, Inc., dated Sep. 7, 2016, 3 pages.

Die Yang, "Dynamics of Capillary-Driven Flow in Open Microchannels," Journal of Physical Chemistry C, Aug. 16, 2011, vol. 115. pp. 18761-18769.

English Translation of Japanese Office Action received for Patent Application No. 2015-524399; Applicant: Tasso, Inc., dated Aug. 8, 2017, 13 pages.

Australian First Patent Examination Report received for Patent Application No. 2015295983; Applicant: Tasso, Inc., dated Jun. 18, 2019, 6 pages.

English Translation of Chinese Office Action received for Patent Application No. 201580053311.7; Applicant: Tasso, Inc., dated May 5, 2019, 18 pages.

Second Examination Report received for European Patent Application No. 15827298.9; Applicant: Tasso, Inc., dated Jul. 4, 2019, 6 pages.

English Translation of Chinese Office Action received for Patent Application No. 201680082347.2; Applicant: Tasso, Inc., dated Aug. 12, 2020, 16 pages.

Extended Supplementary European Search Report received for EP Application No. 16880039.9; Applicant: Tasso, Inc, dated May 8, 2019, 10 pages.

Australian Examination Report issued for Australian Application No. 2015295983; Applicant: Tasso, Inc., dated Jun. 18, 2019, 6 pages.

English translation of Chinese Office Action issued for Chinese Application No. 201580053311.7; Applicant: Tasso, Inc., dated May 5, 2019, 18 pages.

First European Examination Report issued for European Application No. 15827298.9; Applicant: Tasso, Inc., dated Aug. 10, 2018, 7 pages.

Intention to Grant received for European Application No. 15827298.9; Applicant: Tasso, Inc., dated Mar. 10, 2020, 5 pages.

International Preliminary Report on Patentability received for PCT Application No. PCT/US2015/043472; Applicant: Tasso, Inc., dated Feb. 16, 2017, 9 pages.

International Search Report and Written Opinion received for PCT Application No. PCT/US2015/043472; Applicant: Tasso, Inc., dated Nov. 12, 2015, 16 pages.

Extended Supplementary European Search Report received for EP Application No. 19861013.1; Applicant: Tasso, Inc, dated Apr. 11, 2022, 10 pages.

\* cited by examiner

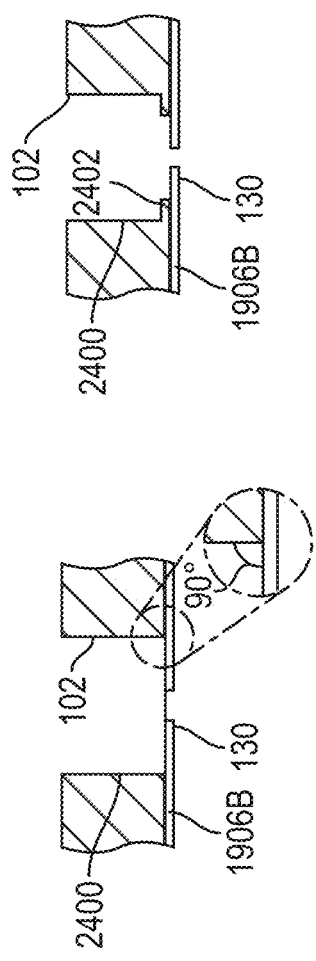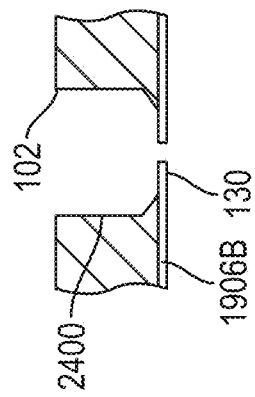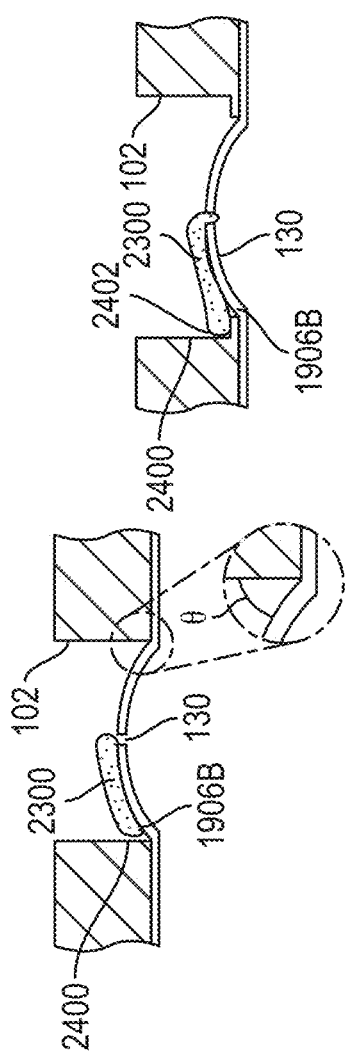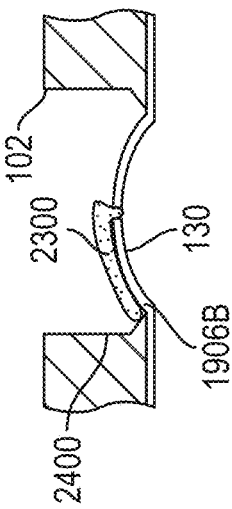

BODILY FLUID COLLECTION DEVICES AND RELATED METHODS

CROSS REFERENCE TO RELATED APPLICATION(S)

This is a continuation of U.S. patent application Ser. No. 16/571,028, filed on Sep. 13, 2019, and titled "BODILY FLUID COLLECTION DEVICES AND RELATED METHODS," which claims the benefit of U.S. Provisional Patent Application No. 62/731,728, filed on Sep. 14, 2018, and titled "BODILY FLUID COLLECTION DEVICES AND RELATED METHODS," each of which is herein incorporated by reference in its entirety.

APPLICATIONS INCORPORATED BY REFERENCE

This application is related to U.S. application Ser. No. 13/750,526, filed Jan. 25, 2013, entitled "Handheld Device for Drawing, Collecting, and Analyzing Bodily Fluid"; U.S. application Ser. No. 13/949,108, filed Jul. 23, 2013, entitled "Methods, Systems, and Devices Relating to Open Microfluidic Channels"; U.S. application Ser. No. 14/816,994, filed Aug. 3, 2015, entitled "Devices, Systems and Methods for Gravity-Enhanced Microfluidic Collection, Handling and Transferring of Fluids"; U.S. application Ser. No. 15/387,177, filed Dec. 21, 2016, entitled "Devices, Systems and Methods for Actuation and Retraction in Fluid Collection"; U.S. application Ser. No. 15/711,746, filed Sep. 21, 2017, entitled "Methods for Delivery of Bodily Fluids Onto a Fibrous Substrate"; and U.S. Provisional Application No. 62/533,323, filed Jul. 17, 2017, entitled "Apparatus, Systems and Methods for Preparing and Shipping"; all of which are incorporated herein by reference in their entireties.

FEDERALLY SPONSORED RESEARCH OR DEVELOPMENT

This invention was made with government support under Contract #HDTRA1-17-C-0066 awarded by the Defense Threat Reduction Agency (DTRA). The government has certain rights in the invention.

TECHNICAL FIELD

The present technology is related to collecting bodily fluid from a patient. In particular, various embodiments of the present technology are related to handheld bodily fluid collection devices and related methods.

BACKGROUND

Devices, systems and methods to collect bodily fluids, such as blood, are widely used in personalized, clinical and field medical applications. Biological samples are commonly collected using simple lancing devices or more sophisticated devices that require trained personnel (e.g., phlebotomy venipunctures). Transferring bodily fluids to a container, receptacle or an analysis device often requires several steps, which can be time consuming, prone to error and/or cumbersome. Moreover, many personalized devices designed for untrained users can obtain only very limited volumes of bodily fluid, which in turn limits the applicability of such devices.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

FIGS. 24A-24F are cross-sectional views of housing features to control flow of bodily fluid along the flexible membrane in accordance with embodiments of the present technology.

DETAILED DESCRIPTION

Devices and methods in accordance with the present technology can be configured to deploy a skin-piercing feature toward a patient's skin to withdraw bodily fluid (e.g., blood). In some embodiments, the devices and methods disclosed herein use an actuation mechanism that deploys the skin-piercing feature in response to movement of an actuator. In some embodiments, the devices and methods disclosed herein use a vacuum mechanism configured to dynamically generate a vacuum that is applied to the patient's skin to facilitate collection of the bodily fluid. In some embodiments, the devices and methods disclosed herein use a flexible membrane that interfaces with the patient's skin and/or bodily fluid for more efficient withdrawal of bodily fluid. The devices and methods of the present technology can be used to quickly and easily obtain a volume of bodily fluid sufficient for downstream testing and analysis.

Specific details of the present technology are described herein with reference to FIGS. 1A-25F. It should be noted that other embodiments in addition to those disclosed herein are within the scope of the present technology. Further, some embodiments of the present technology can have different configurations, components, and/or procedures than those shown or described herein. Moreover, a person of ordinary skill in the art will understand that some embodiments of the present technology can have configurations, components, and/or procedures in addition to those shown or described herein and that these and other embodiments can be without several of the configurations, components, and/or procedures shown or described herein without deviating from the present technology.

The headings provided herein are for convenience only and should not be construed as limiting the subject matter disclosed.

I. BODILY FLUID COLLECTION DEVICE

Figure 1A:
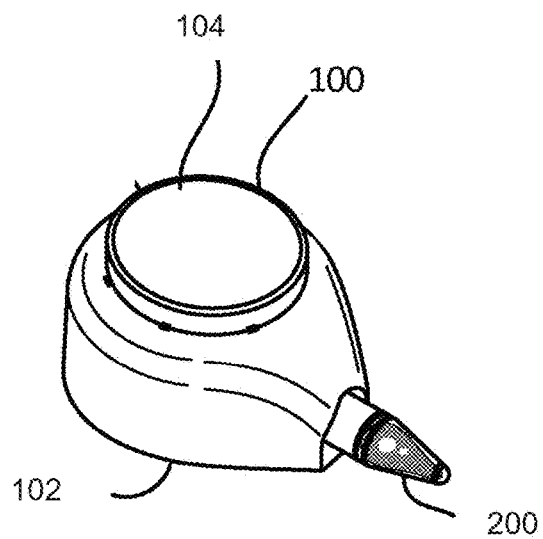
FIG. 1A is a perspective view of a bodily fluid collection device configured in accordance with an embodiment of the present technology.

FIG. 1A is a perspective view of a bodily fluid collection device 100 ("device 100") configured in accordance with an embodiment of the present technology. The device 100 can be handheld with a size that is easily grasped and manipulated by one or both of a patient's hands. Such handheld devices advantageously allow a patient to collect a bodily fluid sample (e.g., a blood sample) without assistance from another individual. In some embodiments, the handheld devices of the present technology can be operated by a layperson outside of a medical setting (e.g., at home or in a field clinic) and without aid of a medical professional.

As shown in FIG. 1A, the device 100 includes a housing 102 and an actuator 104. The actuator 104 (e.g., a button) is movable relative to the housing 102 to actuate withdrawal of a bodily fluid from the patient. The housing 102 is removably coupled to a collection reservoir 200 (e.g., a tube or cartridge) for receiving the bodily fluid withdrawn from the patient. The reservoir 200 can act as a removable and standardized container for bodily fluid that can be detached and inserted into clinical and laboratory equipment or workflows, e.g., for diagnostics and/or biomarker detection.

Figure 1B:
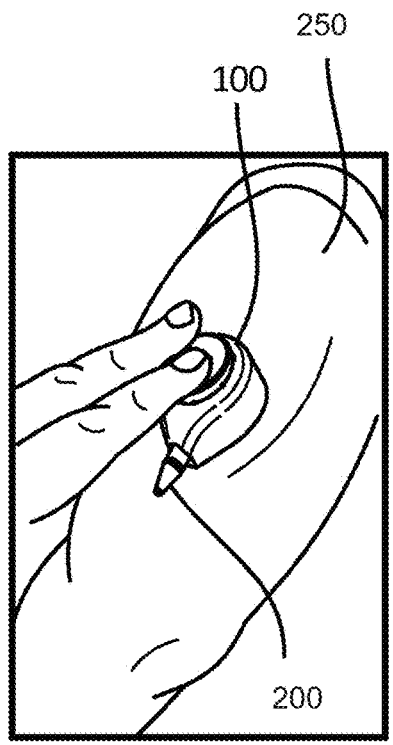
FIG. 1B is a perspective view of the bodily fluid collection device of FIG. 1A in use.

FIG. 1B is a perspective view of the bodily fluid collection device 100 in use. To collect a bodily fluid sample, the device 100 is applied to a patient's body, with the bottom surface of the housing 102 positioned against the skin 250 and the actuator 104 positioned away from the skin 250. Pressing the actuator 104 deploys a skin-piercing feature (e.g., a lancet, blade, or needle) from within the device 100 to pierce the skin 250. Subsequent retraction of the actuator 104 away from the skin creates a vacuum within the device 100 that acts against the patient's skin either directly or indirectly. Bodily fluid from the resulting incision is withdrawn into the housing 102 and collected into the reservoir 200.

Figure 1C:
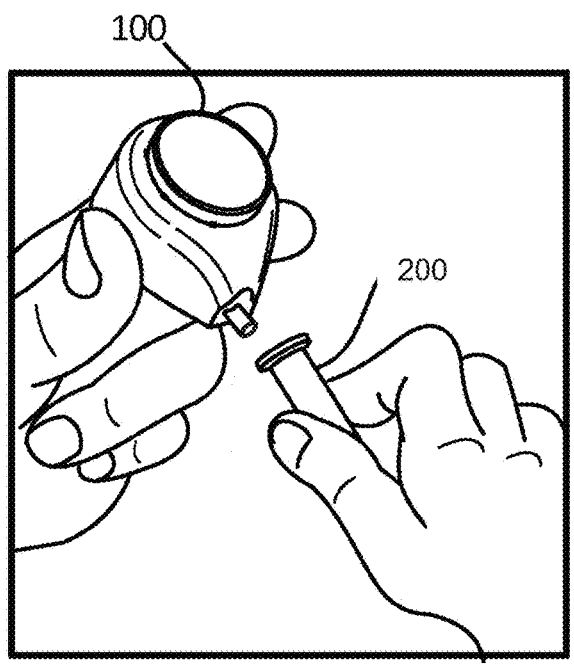
FIG. 1C is a perspective view illustrating detachment of the collection reservoir from the bodily fluid collection device of FIG. 1A.

FIG. 1C is a perspective view illustrating detachment of the collection reservoir 200 from the bodily fluid collection device 100. Once the desired amount of bodily fluid has been collected into the reservoir 200, the device 100 is removed from the skin 250, and the reservoir 200 is detached from the housing 102.

Figure 2A:
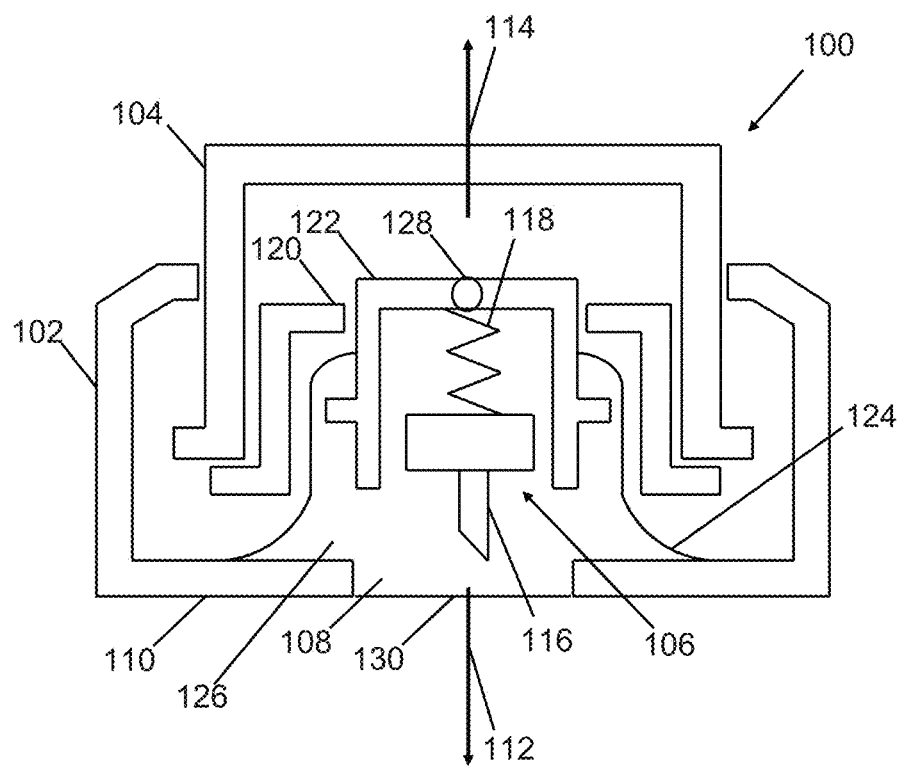
FIG. 2A is a schematic cross-sectional illustration of a bodily fluid collection device configured in accordance with an embodiment of the present technology.

FIG. 2A is a schematic cross-sectional illustration of a bodily fluid collection device 100 configured in accordance with an embodiment the present technology. The device 100 includes the housing 102, the actuator 104, a skin-piercing assembly 106 located at least partially or completely within the housing 102, and an opening 108 through the housing 102. In some embodiments, the opening 108 is formed in a bottom surface 110 of the housing 102 such that the opening 108 is against the skin when the device 100 is applied to a patient's body. The actuator 104 is movable relative to the housing 102 along a deployment direction 112 and a retraction direction 114. The deployment direction 112 can be a downward direction in the orientation of FIG. 2A, e.g., toward the opening 108, and the retraction direction 114 can be an upward direction, e.g., away from the opening 108. The deployment direction 112 is generally toward the skin, while the retraction direction 114 is generally away from the skin.

The skin-piercing assembly 106 includes at least one skin-piercing feature 116 (e.g., a lancet, blade, or needle) and a biasing member 118 (e.g., a spring) that is coupled to the skin-piercing feature 116. The biasing member 118 is configured to drive the skin-piercing feature 116 along the deployment direction 112 toward the opening 108. The skin-piercing feature 116 can be configured to pierce the patient's skin to create an incision from which bodily fluid can be withdrawn. The size of the skin-piercing feature can be varied as desired. For example, a relatively large skin-piercing feature can be advantageous for creating a larger incision that allows for withdrawal of larger volumes of bodily fluid. A relatively small skin-piercing feature can be advantageous for reducing pain and achieving high penetration velocities. Optionally, the skin-piercing assembly 106 can include a plurality of skin-piercing features, e.g., two, three, four, five, or more skin-piercing features. In some embodiments, the device 100 can include a corresponding number of openings 108, such that each skin-piercing feature passes through a respective opening to pierce the patient's skin. However, more than one skin piercing feature 116 can pass through an opening 108. For example, all of the skin piercing features 116 can pass through a single opening 108.

Figure 2B:
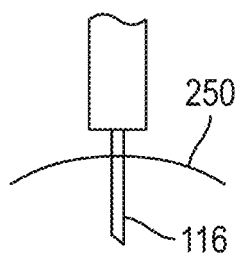
FIG. 2B is a side view of a skin-piercing feature configured in accordance with the present technology.

FIG. 2B is a side view of the skin-piercing feature 116 of the device 100 configured in accordance with an embodiment the present technology. The length of the skin-piercing feature 116 can be selected to produce an appropriate penetration depth into the skin 250. For example, the skin-piercing feature 116 can have a length of about 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, or 4.0 mm. The length of the skin-piercing feature 116 can be selected to produce a penetration depth less than or equal to about 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, or 4.0 mm below the surface of the skin 250.

Figure 2C:
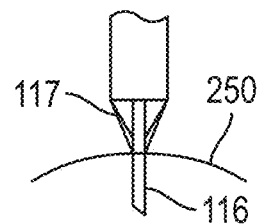
FIG. 2C is a side view of a skin-piercing feature with a stop feature configured in accordance with the present technology.

FIG. 2C is a side view of the skin-piercing feature 116 with a stop feature 117 configured in accordance with an embodiment the present technology. In some embodiments, the stop feature 117 is at or near the base of the skin-piercing feature 116 to limit the penetration depth of the skin-piercing feature 116 into the skin. For example, the stop feature 117 can limit the penetration depth to less than or equal to about 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, or 4.0 mm below the surface of the skin 250.

Referring back to FIG. 2A, the device 100 includes an actuation mechanism for actuating the deployment of the skin-piercing assembly 106. For example, the actuator 104 can be mechanically coupled to the skin-piercing assembly 106, e.g., via a platform 120 and a plunger 122, to deploy the skin-piercing feature along the deployment direction 112. In the depicted embodiment, the platform 120 is located at least partially within the actuator 104, the plunger 122 is located at least partially within the platform 120, and the skin-piercing assembly 106 is coupled to the plunger 122. Optionally, the actuation mechanism can also actuate the retraction of the skin-piercing feature 116 along the retraction direction 114, after the skin-piercing feature 116 has been deployed. Additional features and implementations of the actuation mechanism are described herein with reference to FIGS. 4-12C.

In some embodiments, the device 100 includes a vacuum mechanism to facilitate collection of the bodily fluid. For example, the device 100 can include a sealing member 124 (e.g., a flexible membrane that can bend and/or is elastic) over the opening 108 to form a lumen 126. The device 100 can include at least one valve 128 fluidically connected to the lumen 126 to control air flow into and out of the lumen 126. The sealing member 124 can be mechanically coupled to the skin-piercing assembly 106, e.g., via the plunger 122, such that movement of the skin-piercing assembly 106 along the deployment direction 112 decreases the volume of the lumen 126, and movement of the skin-piercing assembly 106 along the retraction direction 114 increases the volume of the lumen 126. The valve 128 can be a one-way valve that permits air to escape from within the lumen 126, e.g., as the lumen volume decreases, but prevents air from entering the lumen 126, e.g., as the lumen volume increases. This creates a low-pressure region (e.g., a vacuum) within the lumen 126 that acts directly or indirectly against the skin. Additional features and implementations of the vacuum mechanism are described herein with reference to FIGS. 13A-18B.

In some embodiments, the device 100 includes a skin interface that interacts with the patient's skin and/or bodily fluid to facilitate collection of the bodily fluid. The skin interface can control the curvature of the skin to maintain the incision in an open position, thus promoting flow of the bodily fluid from the skin. The skin interface can also include surface features and/or treatments to direct flow of the bodily fluid toward a desired location, e.g., into the housing 102 and toward the collection reservoir. For example, the device 100 can include a flexible membrane 130 coupled to the housing 102 and covering at least a portion of the opening 108. The flexible membrane 130 can be bendable and/or stretchable (e.g., elastic). The flexible membrane 130 can be coupled to the bottom surface 110 of the housing 102, such that the membrane 130 is on the exterior of the housing 102. Alternatively, the flexible membrane 130 can be within the interior of the housing 102. The flexible membrane 130 can optionally include an aperture to allow the skin-piercing feature 116 to pass through. The flexible membrane 130 can be made of an elastic material (e.g., polyurethane, silicone) that deforms into a curved shape when exposed to a vacuum. When the device 100 is applied to the patient's body, the flexible membrane 130 can form a seal against the patient's skin to control the skin curvature and/or direct flow of the bodily fluid from the skin. Additional features and implementations of skin interfaces are described herein with reference to FIGS. 19A-25F.

Figure 3:
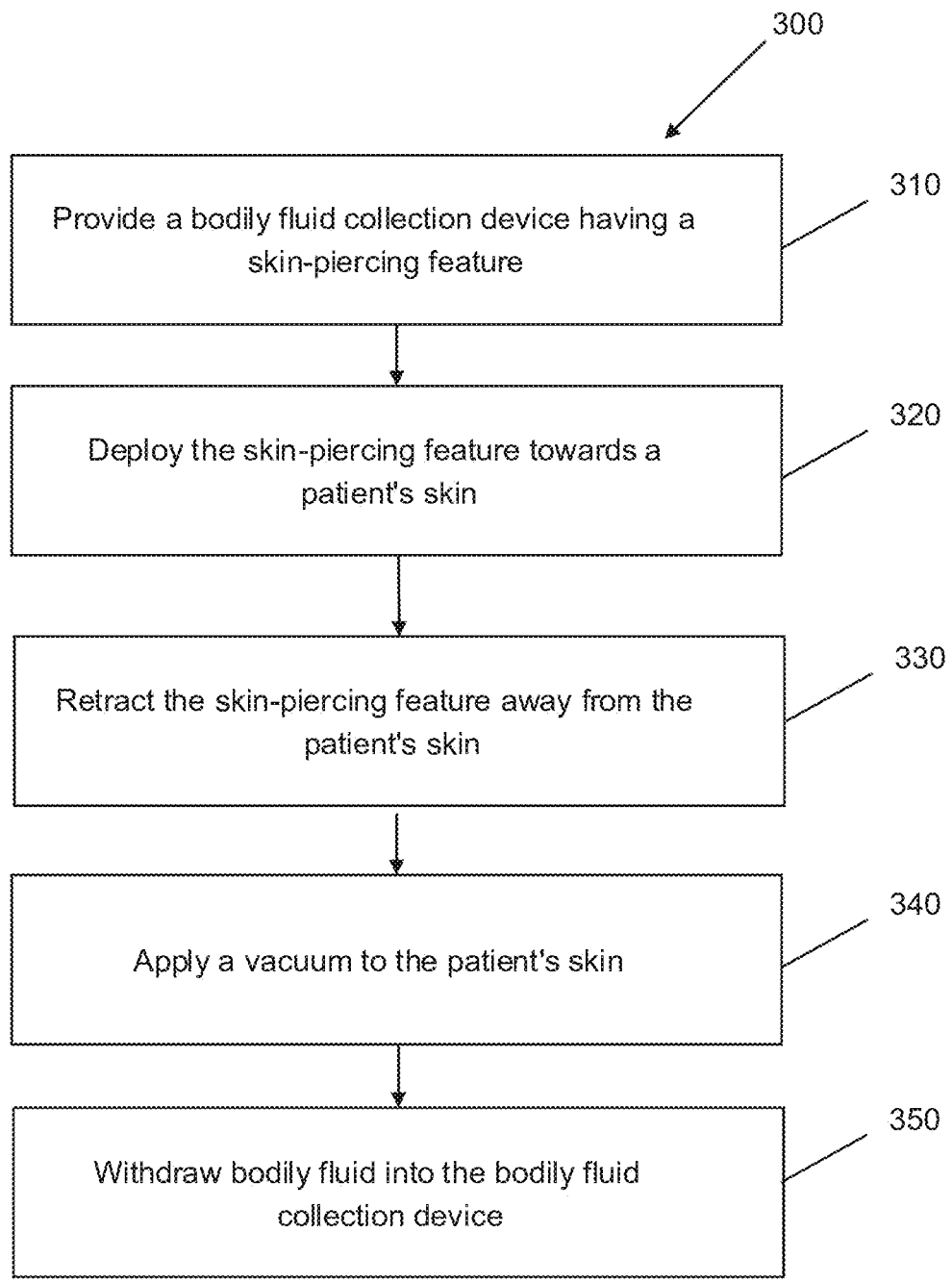
FIG. 3 is a block diagram of a method for using a bodily fluid collection device in accordance with an embodiment of the present technology.

FIG. 3 is a block diagram of a method 300 for using a bodily fluid collection device configured in accordance with an embodiment the present technology. Although various steps of the method 300 are described with respect to the components of the device 100, it shall be appreciated that the method 300 is generally applicable to any embodiment of the bodily fluid collection devices disclosed herein.

The method 300 includes providing a bodily fluid collection device having a skin-piercing feature (block 310) and deploying the skin-piercing feature toward a patient's skin (block 320). The deployment of the skin-piercing feature can be driven by an actuation mechanism, as described herein with reference to FIGS. 4-12C. In some embodiments, the actuation mechanism includes an actuator mechanically coupled to the skin-piercing assembly, such that movement of the actuator along the deployment direction drives the skin-piercing feature to be deployed toward the opening along the deployment direction. For example, in the embodiment of FIG. 2A, the actuator 104 engages and moves the platform 120 along the deployment direction 112, the platform 120 engages and moves the plunger 122 along the deployment direction 112, and the movement of the plunger 122 along the deployment direction 112 causes the skin-piercing feature 116 to be deployed. In some embodiments, the movement of the plunger 122 along the deployment direction 112 releases a load on the biasing member 118, thus causing the biasing member 118 to actively drive the skin-piercing feature 116 along the deployment direction 112. In some embodiments, the biasing member 118 is not initially loaded, but movement of the actuator 104, platform 120, and plunger 122 loads the biasing member 118 with a stored energy until the actuator reaches a trigger point that releases the skin-piercing feature 116. This allows the stored energy in the biasing member 118 to be quickly released and thereby drive the skin-piercing feature 116 at a high velocity into the skin. This approach is expected to allow for easier device assembly, improve device stability and safety, increase device shelf life, and reduce fatigue on the biasing member.

The skin-piercing feature can be deployed at any velocity suitable for creating an incision in the patient's skin for withdrawing bodily fluid. As used herein, "velocity" may refer to a maximum velocity, an average velocity, or a velocity at the time the skin-piercing feature contacts the skin. In some embodiments, the skin-piercing feature is deployed at a velocity greater than or equal to about 0.1 m/s, 0.2 m/s, 0.3 m/s, 0.4 m/s, 0.5 m/s, 0.6 m/s, 0.7 m/s, 0.8 m/s, 0.9 m/s, 1.0 m/s, 1.5 m/s, 2.0 m/s, or 2.5 m/s. In some embodiments, the skin-piercing feature is deployed at a velocity less than or equal to about 0.1 m/s, 0.2 m/s, 0.3 m/s, 0.4 m/s, 0.5 m/s, 0.6 m/s, 0.7 m/s, 0.8 m/s, 0.9 m/s, 1.0 m/s, 1.5 m/s, 2.0 m/s, or 2.5 m/s. In some embodiments, the skin-piercing feature is deployed at a velocity within a range from about 0.1 m/s to about 2.5 m/s.

In some embodiments, the skin-piercing feature is deployed at a high velocity, e.g., a velocity greater than or equal to about 2.5 m/s. High velocity deployment of the skin-piercing feature can produce more effective penetration for some skin types with low stiffness or elasticity, create a larger incision that permits withdrawal of a larger volume of bodily fluid, or allow the use of the device on other mammalian species other than humans. Alternatively, in some embodiments, the skin-piercing feature is deployed at a low velocity, e.g., a velocity less than or equal to about 0.1 m/s. Low velocity deployment of the skin-piercing feature can reduce the pain experienced by the patient.

The method 300 further includes retracting the skin-piercing feature away from the patient's skin (block 330). The skin-piercing feature can be retracted by an actuation mechanism, as described herein with reference to FIGS. 4-12C. The skin-piercing feature can be retracted at least partially or completely into the housing along the retraction direction. In some embodiments, the skin-piercing feature is retracted automatically after deployment such that the patient does not need to perform any additional actions for retraction to occur. Optionally, the skin-piercing feature is locked into the retracted position such that further movement of the actuator along the deployment direction does not re-deploy the skin-piercing feature.

The method 300 further includes applying a vacuum to the patient's skin (block 340). For example, the device can include a vacuum mechanism that generates the vacuum contemporaneously with the deployment and retraction of the skin-piercing feature, as described herein with reference to FIGS. 13A-18B. For example, in the embodiment of FIG. 2, movement of the plunger 122 along the deployment direction 112 decreases the volume of the lumen 126. Air can escape from within the lumen 126 via the valve 128 as the volume decreases. When the plunger 122 is moved along the retraction direction 114, the volume of the lumen 126 increases, while the valve 128 prevents air from entering the lumen 126. Accordingly, the pressure within the lumen 126 decreases, creating a vacuum within the lumen 126 that draws the bodily fluid and/or a portion of the patient's skin through the opening 108. In some embodiments, the valve can be mechanically shutoff as the plunger 122 reaches desired displacement position, such as the further-most displacement position. This is expected to increase the amount of bodily fluid withdrawn from the skin by opening local capillaries and maintaining the incision in an open configuration.

The method 300 further includes withdrawing bodily fluid into the bodily fluid collection device (block 350). Once the skin-piercing feature has formed an incision in the patient's skin, bodily fluid from the incision is drawn into the housing through the opening and into a collection reservoir. Optionally, the device can include a skin interface (e.g., a flexible membrane) that interacts with the skin and/or bodily fluid to enhance flow of the bodily fluid into the device, as described herein with reference to FIGS. 19A-25F. In some embodiments, a flexible membrane is expected to provide improved control over larger areas of skin, thus allowing the device to access more capillaries and increase the volume of bodily fluid that can be withdrawn, as well as provide a support to collect blood close to the incision point to prevent or at least mitigate the blood from travelling on the skin of the user. This further allows the delivery of anticoagulant material rapidly after the blood is extracted from the capillaries.

The amount of bodily fluid withdrawn into the device, also known as the "draw volume," can be sufficiently large for downstream testing and analysis of the bodily fluid, e.g., for diagnostics and/or biomarker detection performed on a blood sample. As used herein, draw volume can refer to the maximum volume of bodily fluid that can be collected from a specified percentage of the patient population, e.g., from at least 90% of patients. The draw volume of the device can be at least about 50 µL, 75 µL, 100 µL, 125 µL, 150 µL, 175 µL, 200 µL, 225 µL, 250 µL, 275 µL, 300 µL, 325 µL, 350 µL, 375 µL, 400 µL, 425 µL, 450 µL, 475 µL, 500 µL, 550 µL, 600 µL, 650 µL, 700 µL, 750 µL, 800 µL, 850 µL, 900 µL, 950 µL, 1 mL, 1.5 mL, or 2 mL of the bodily fluid from the patient. In some embodiments, the draw volume of the device is up to about 50 µL, 75 µL, 100 µL, 125 µL, 150 µL, 175 µL, 200 µL, 225 µL, 250 µL, 275 µL, 300 µL, 325 µL, 350 µL, 375 µL, 400 µL, 425 µL, 450 µL, 475 µL, 500 µL, 550 µL, 600 µL, 650 µL, 700 µL, 750 µL, 800 µL, 850 µL, 900 µL, 950 µL, 1 mL, 1.5 mL, or 2 mL of the bodily fluid from the patient. In some embodiments, the draw volume of the device is within a range from about 50 µL to about 2 mL, from about 100 µL to about 2 mL, from about 100 µL to about 1.5 mL, from about 100 µL to about 1 mL, or from about 100 µL to about 500 µL.

II. ACTUATION MECHANISM

The bodily fluid collection devices of the present technology can include an actuation mechanism that deploys the skin-piercing assembly. In some embodiments, the actuation mechanism includes an actuator that is mechanically coupled to the skin-piercing assembly, such that movement of the actuator causes a skin-piercing feature of the skin-piercing assembly to be deployed along a deployment direction toward the patient's skin. The actuator movement that deploys the skin-piercing feature can be a simple, unidirectional movement that is easily performed by a layperson, such as pressing a button.

The actuation mechanism can include a biasing member (e.g., a spring) that is coupled to the skin-piercing feature to drive the skin-piercing feature along a deployment direction. The biasing member can have an unloaded state (e.g., an uncompressed state), in which little or no load is placed on the biasing member (e.g., little or no energy is stored in the biasing member), and a loaded state (e.g., a compressed state), in which a load is placed on the biasing member (e.g., sufficient energy to drive the skin-piercing feature 116 at a desired velocity is stored in the biasing member). When the load on the biasing member is released, the biasing member transitions from the loaded state to the unloaded state, and the transition of the biasing member to the unloaded state drives the deployment of the skin-piercing feature in the deployment direction.

In some embodiments, the actuation mechanism is configured such that moving the actuator along the deployment direction both applies and releases a load on the biasing member ("in situ loaded"). An in situ loaded actuation mechanism may include little or no load on the biasing member before moving the actuator from an initial position along the deployment direction. For example, the load on the biasing member before moving the actuator can be less than or equal to about 15%, 10%, 5%, or 1% of the maximum load on the biasing member during operation of the bodily fluid collection device. As another example, the length of the biasing member before moving the actuator from the initial position can be at least about 85%, 90%, 95%, or 99% of its unloaded length. Advantages of an in situ loaded actuation mechanism include easier device assembly, improved device stability and safety, longer device shelf life, and reduced fatigue on the biasing member.

Figure 4:
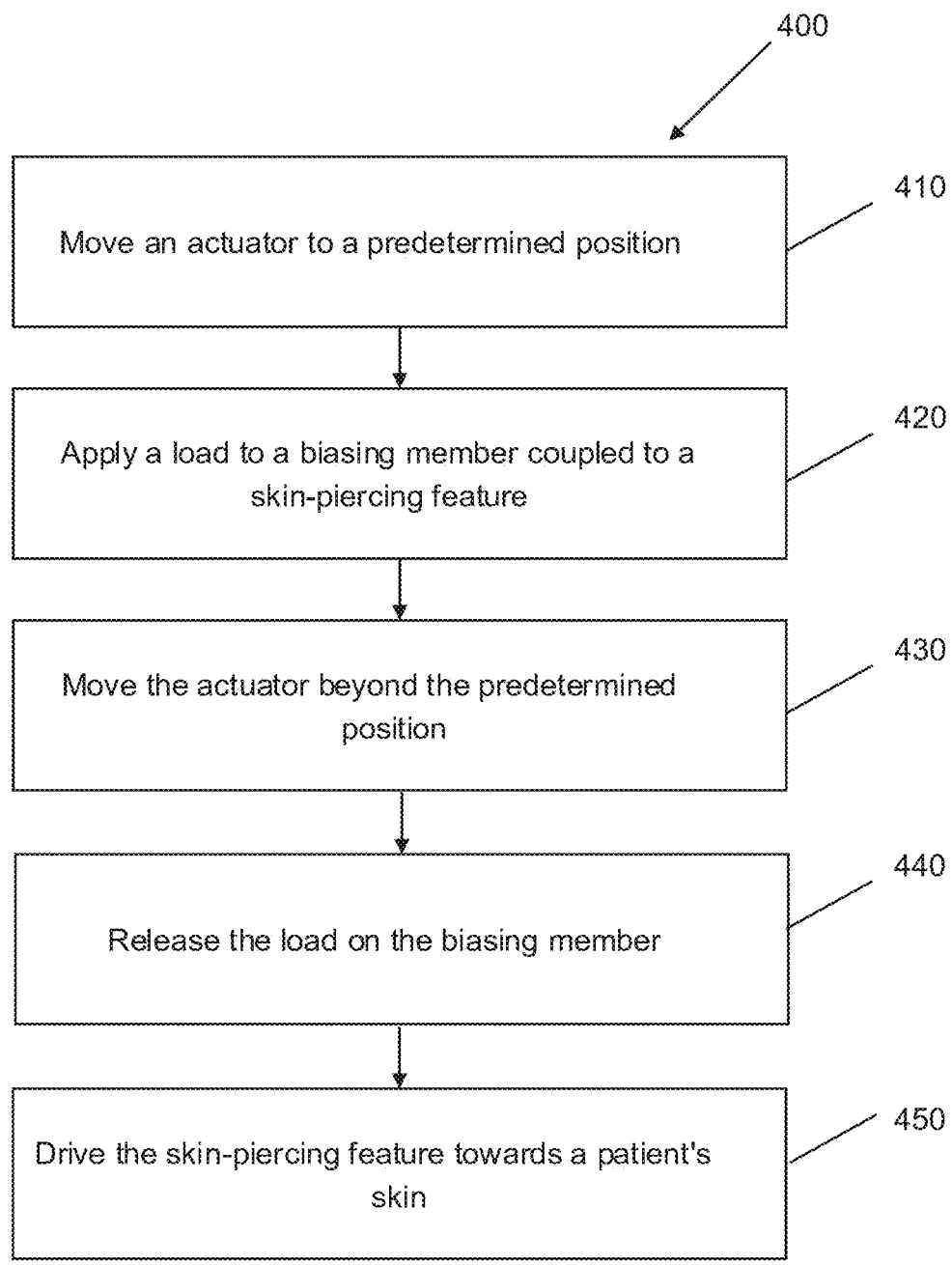
FIG. 4 is a block diagram of a method for deploying a skin-piercing feature using an in situ loaded actuation mechanism configured in accordance with an embodiment of the present technology.

FIG. 4 is a block diagram of a method 400 for deploying a skin-piercing feature using an in situ loaded actuation mechanism configured in accordance with an embodiment the present technology. The method 400 can be applied to any of the bodily fluid collection devices disclosed herein, such as the device 100. Additionally, one or more steps of the method 400 can be combined with or substituted for any of the steps of the other methods disclosed herein. For example, one or more steps of the method 400 can be performed in combination with or as sub-steps of block 320 of the method 300.

The method 400 includes moving an actuator to a predetermined position (block 410). The predetermined position can be a position along a deployment direction (e.g., toward the patient's skin). For example, a patient can press the actuator once the bodily fluid collection device has been applied to the skin. In some embodiments, the predetermined position is at least about 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, 10 mm, 15 mm, or 20 mm from an initial resting position of the actuator.

The method further includes applying a load to a biasing member coupled to a skin-piercing feature (block 420). The load can be applied to the biasing member by the movement of the actuator along the deployment direction to the predetermined position. The biasing member can initially be in an unloaded state with little or no applied load, and moving the actuator can increase the load on the biasing member to at least a partially loaded state, or to a fully loaded state. In some embodiments, the actuator is mechanically coupled to the biasing member to apply the load on the biasing member, e.g., by compressing the biasing member. For example, the biasing member can be compressed to a loaded length that is less than or equal to about 5%, 10%, 15%, 20%, 25%, 30%, 35%, 40%, 45%, 50%, 55%, 60%, 65%, 70%, 75%, or 85% of its unloaded length.

The method next includes moving the actuator beyond the predetermined position (block 430). For example, the actuator can be moved to a position that is further along the deployment direction than the predetermined position, e.g., by the patient continuing to press on the actuator while the device is applied to the skin. In some embodiments, the actuator is moved beyond the predetermined position by a distance of at least about 0.1 mm, 0.5 mm, 1 mm, 1.5 mm, 2 mm, 2.5 mm, 3 mm, 3.5 mm, 4 mm, 4.5 mm, or 5 mm.

The method also includes releasing the load on the biasing member (block 440). The load can be released by moving the actuator along the deployment direction beyond the predetermined position. The method further includes driving the skin-piercing feature toward a patient's skin (block 450). The skin-piercing feature can be collectively driven toward the patient's skin by both the actuator and the biasing member. In some embodiments, moving the actuator along the deployment direction beyond the predetermined position releases the load on the biasing member so that the biasing member actively drives the skin-piercing feature along the deployment direction. For example, the biasing member can drive the skin-piercing feature as the biasing member extends from a compressed state toward an uncompressed state.

Figure 5A:
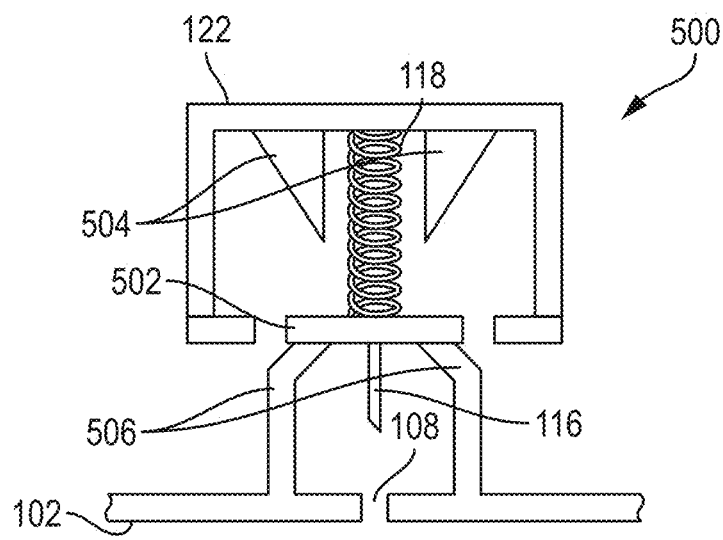
FIGS. 5A-5C are schematic cross-sectional illustrations of the operation of an in situ loaded actuation mechanism configured in accordance with an embodiment the present technology.
Figure 5B:
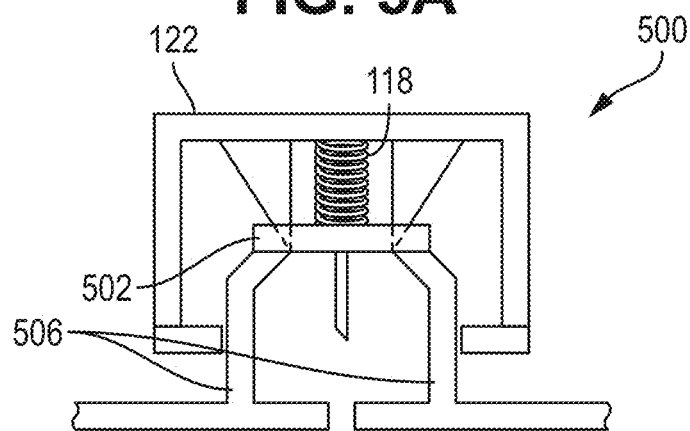
Figure 5C:
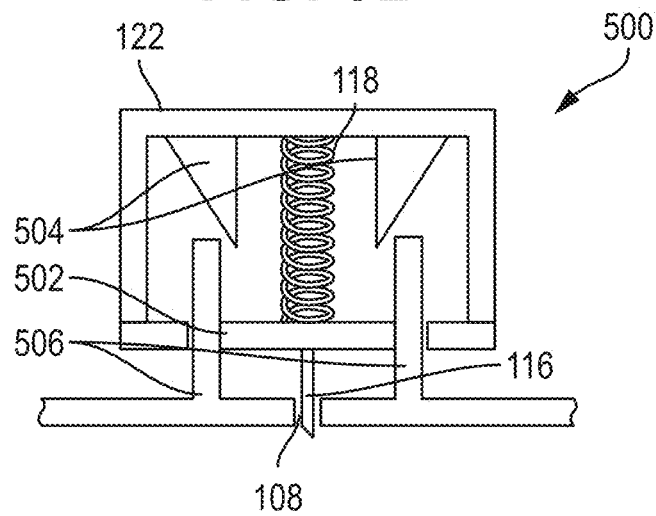

FIGS. 5A-5C are schematic cross-sectional illustrations of the operation of an in situ loaded actuation mechanism 500 configured in accordance with an embodiment the present technology. The actuation mechanism 500 includes the biasing member 118, the plunger 122, the housing 102, and the actuator (not shown). The skin-piercing feature 116 is coupled to the biasing member 118 via a base 502. The plunger 122 is positioned around at least a portion of the skin-piercing assembly 106 and includes one or more projections 504. The housing 102 includes the opening 108 and one or more arms 506 within the housing 102.

Before moving the actuator along the deployment direction (FIG. 5A), there is little or no loading on the biasing member 118, such that the biasing member is at or near its uncompressed length. Moving the actuator along the deployment direction up to a predetermined position (FIG. 5B) causes the arm(s) 506 to assume a flexed configuration that engages the base 502 and applies a load to the biasing member 118. For example, in the depicted embodiment, the actuator engages and moves the plunger 122 and skin-piercing assembly 106 downward toward the opening 108. This downward movement brings the arm(s) 506 into engagement with the base 502. The arm(s) 506 are in a flexed configuration (e.g., inwardly bent configuration) that presses up against the base 502, causing the biasing member 118 to be compressed between the base 502 and the plunger 122.

Moving the actuator along the deployment direction beyond the predetermined position (FIG. 5C) causes the arm(s) 506 to flex outward and thereby disengaged from the base 502 (e.g., a resting configuration or release configuration), which in turn releases the load on the biasing member 118. For example, in the depicted embodiment, continued downward movement of the actuator brings the projection(s) 504 of the plunger 122 into contact with the inwardly flexed arm(s) 506. Each projection 504 contacts and displaces a corresponding arm 506 from the inwardly flexed configuration to a released configuration, e.g., by bending the arm 506 outward. Once in the released configuration, the arm(s) 506 disengage from the base 502 and release the compression on the biasing member 118. The biasing member 118 reverts toward its uncompressed length, driving the skin-piercing feature 116 downward toward the opening 108.

The features of the actuation mechanism 500 can be varied as desired. For example, although FIGS. 5A-5C illustrate a mechanism 500 with two projections and two arms, alternative embodiments may include any suitable number of projections and arms. In some embodiments, the mechanism 500 can include one, two, three, four, five, or more projections; and one, two, three, four, five, or more arms. The positioning of the projection(s) 504 and the arm(s) 506 can also be varied. For instance, the projection(s) 504 can be on the housing 102, and the arm(s) 506 can be on the plunger 122. Additionally, although FIGS. 5A-5C illustrate the arm(s) 506 being displaced outward by the projection(s) 504 to release the biasing member 118, in alternative embodiments, the arm(s) 506 may be displaced inward by the projection(s) 504 to release the biasing member 118.

FIGS. 6A-10 illustrate a bodily fluid collection device 100 with an in situ loaded actuation mechanism configured in accordance with an embodiment the present technology. The device 100 includes the housing 102, the actuator 104, and the skin-piercing assembly 106. The housing 102 includes an upper housing portion 602A and a lower housing portion 602B. In some embodiments, the upper housing portion 602A and the lower housing portion 602B are separate components that are coupled together to form the housing 102. In alternative embodiments, the upper housing portion 602A and lower housing portion 602B can be integrally formed as a single unitary component. The upper housing portion 602A is shaped to receive the actuator 104. The lower housing portion 602B includes the bottom surface 110 having the opening 108.

The actuator 104 is at least partially within the upper housing portion 602A of the device 100. In some embodiments, the actuator 104 is a hollow, button-like structure positioned to be depressed by the patient along the deployment direction 112 to deploy the skin-piercing feature 116 of the skin-piercing assembly 106. The actuator 104 can be mechanically coupled to the skin-piercing assembly 106 via one or more internal device components, such as the platform 120, washer 604, sealing member 124, and/or plunger 122. In some embodiments, the actuator 104 is positioned around at least a portion of the platform 120, the platform 120 is positioned around at least a portion of the washer 604, and the washer 604 is positioned around at least a portion of the sealing member 124, and the sealing member 124 is positioned around at least a portion of the plunger 122. The actuator 104, platform 120, washer 604, sealing member 124, and plunger 122 can be concentrically positioned, such that the longitudinal axes (e.g., the axis extending along the deployment direction 112) of these components are aligned.

The actuator 104, platform 120, washer 604, sealing member 124, and plunger 122 can be coupled to each other using any suitable combination of complementary interconnecting features (e.g., notches, grooves, projections, tabs, and the like). In some embodiments, the lower edge 606 of the actuator 104 engages at least one tab feature 608 of the platform 120 when the actuator 104 is moved along the deployment direction 112. The at least one tab feature 608 can extend radially outward from an outer surface of the platform 120 to receive and engage the lower edge 606 of the actuator 104. In some embodiments, the platform 120 includes at least one projecting feature 610 that engages at least one tab feature 612 of the washer 604 when the platform 120 is moved along the deployment direction 112. The at least one projecting feature 610 can extend radially inward from an inner surface of the platform 120, and the at least one tab feature 612 can extend radially outward from an outer surface of the washer 604. Optionally, the washer 604 can include three tab features evenly spaced along the outer surface of the washer 604, as shown in FIGS. 6C-6D. In some embodiments, the lower edge 614 of the washer 604 engages the sealing member 124 and a collar feature 616 of the plunger 122 when the washer 604 is moved along the deployment direction 112. The collar feature 616 can extend radially outward from an outer surface of the plunger 122 to receive and engage the lower edge 614 of the washer 604.

Although the actuator 104, platform 120, washer 604, sealing member 124, and plunger 122 are depicted in FIGS. 6A-6E as being separate components, one or more of these components may also be integrally formed with each other. For example, the sealing member 124 and the plunger 122 can be integrally formed as a single unitary component, e.g., by overmolding. As another example, the washer 604, sealing member 124, and plunger 122 can be integrally formed as a single unitary component, e.g., by overmolding. Such approaches may be beneficial for reducing the number of components to simplify device assembly.

The skin-piercing assembly 106 is mechanically coupled to the plunger 122. In some embodiments, the skin-piercing assembly 106 is coupled to an interior surface of the plunger 122, such that the plunger 122 is around at least a portion of the skin-piercing assembly. The skin-piercing assembly 106 can include the biasing member 118, base 502, and at least one skin-piercing feature 116. The biasing member 118 can have an upper portion coupled to the interior surface of the plunger 122 and a lower portion coupled to the base 502. The skin-piercing feature 116 can be mounted to the base 502.

The device 100 includes at least one arm 506 within the housing 102 near the opening 108. The arm 506 can be integrally formed with the lower housing portion 502B, or can be a separate component that is coupled to the lower housing portion 502B. The arm 506 can be a flexible component that is movable between a flexed configuration (e.g., an inwardly bent configuration) and a resting configuration (e.g., a straightened or outwardly bent configuration).

Figure 6A:
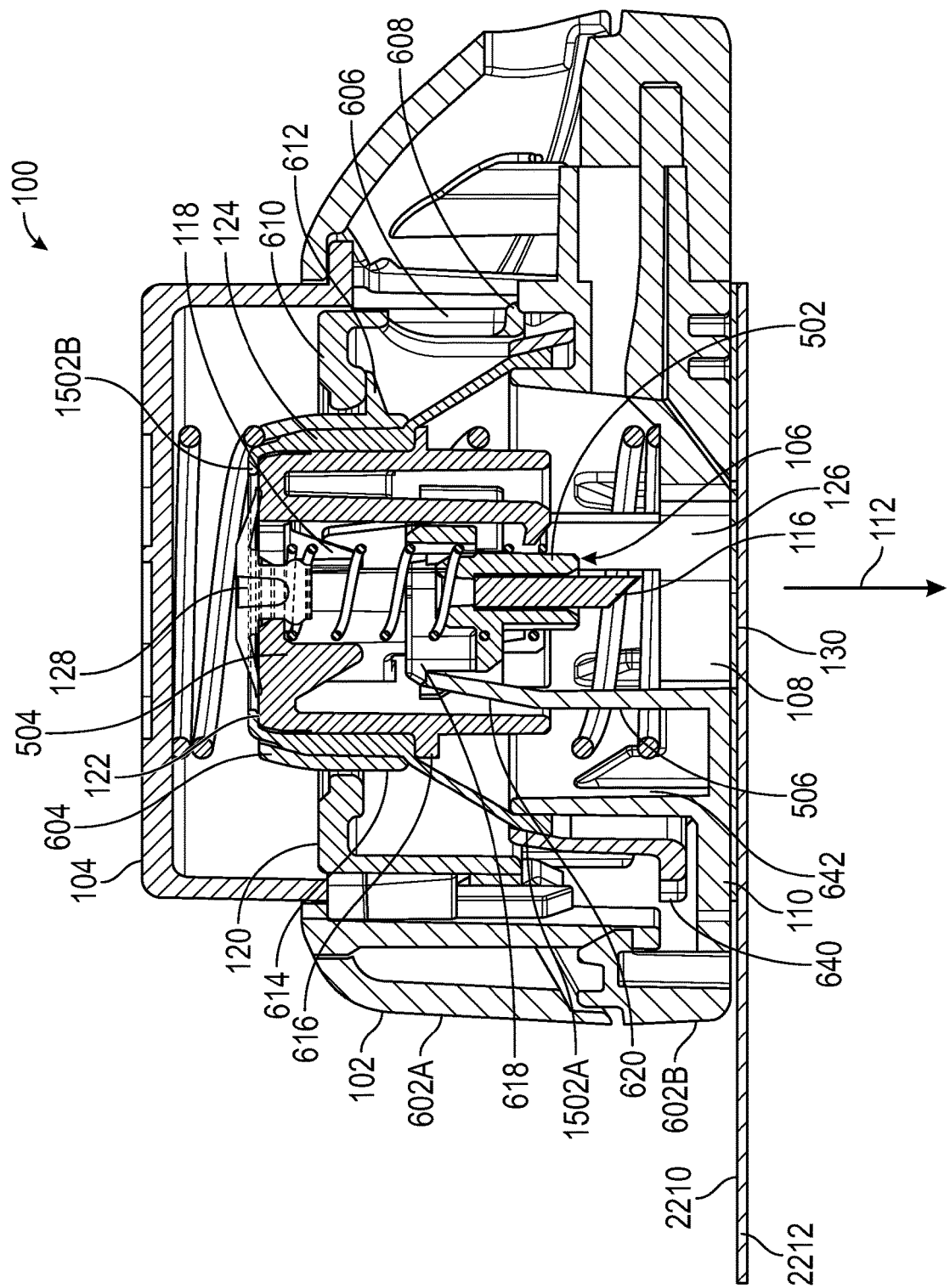
FIG. 6A is a cross-sectional view of a bodily fluid collection device with an in situ loaded actuation mechanism configured in accordance with an embodiment of the present technology.
Figure 6B:
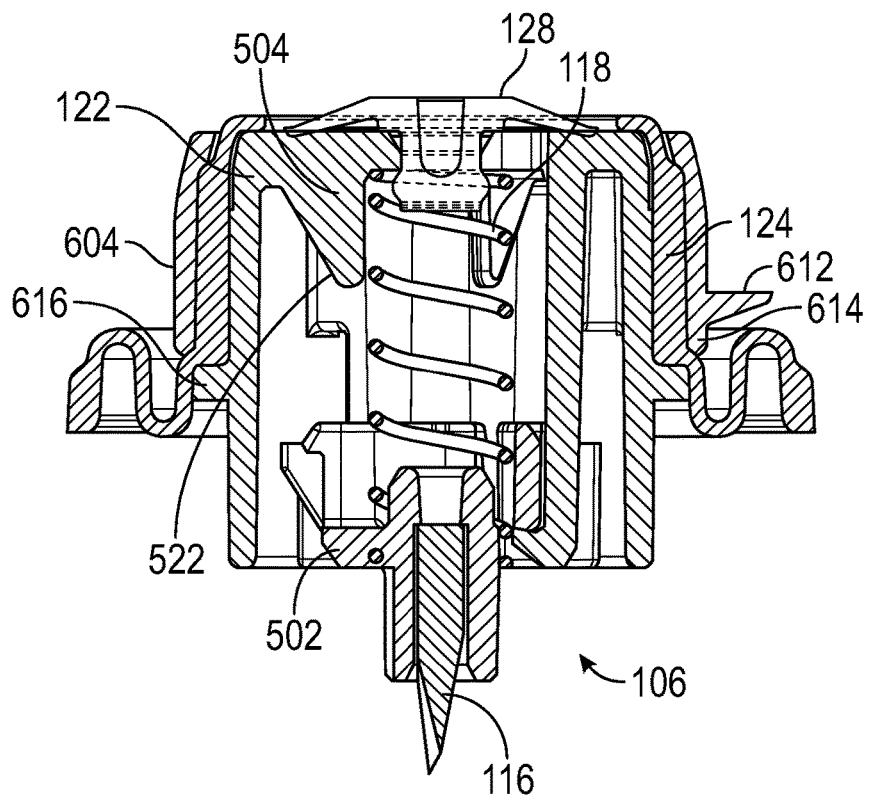
FIG. 6B is a cross-sectional view of internal components of the device of FIG. 6A.
Figure 6C:
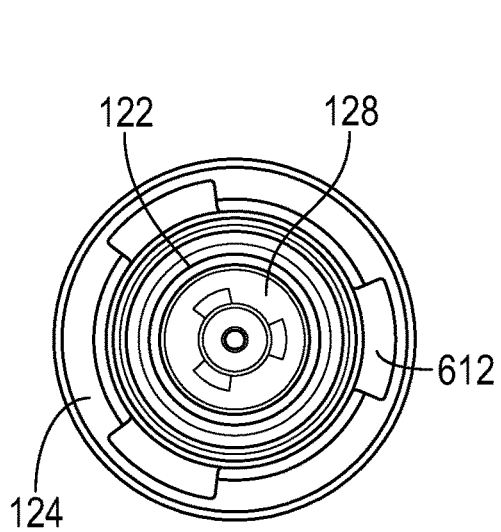
FIG. 6C is a top view of internal components of the device of FIG. 6A.
Figure 6D:
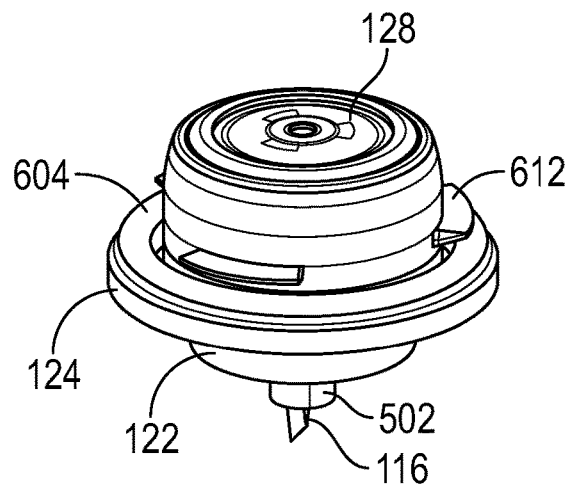
FIG. 6D is a perspective view of internal components of the device of FIG. 6A.
Figure 6E:
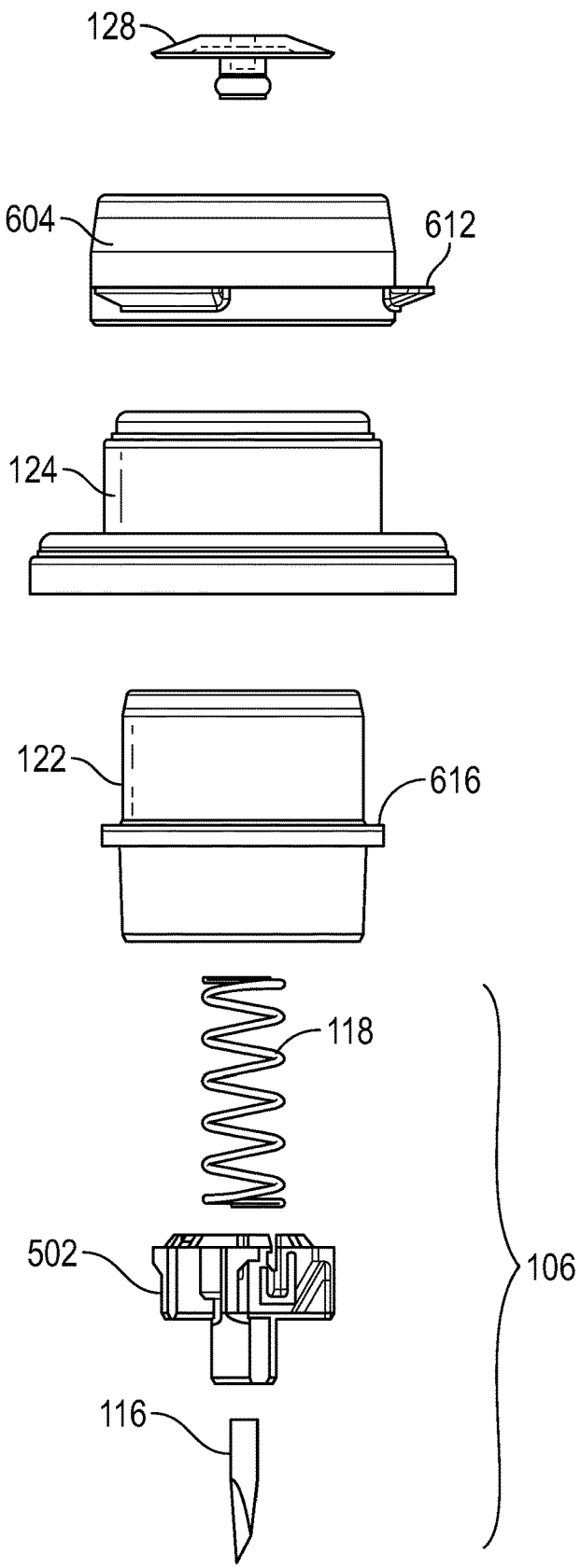
FIG. 6E is an exploded view of internal components of the device of FIG. 6A.

FIG. 6A is a cross-sectional view of the device 100 prior to movement of the actuator 104 along the deployment direction 112 ("pre-actuation state"). In the pre-actuation state, the arm 506 is initially in a flexed configuration engaging the base 502. The base 502 can include a hook feature 618 that receives the end portion 620 of the arm 506. The hook feature 618 can restrain the arm 506 in the flexed configuration and prevent the arm 506 from reverting to the released configuration. When the actuator 104 is moved along the deployment direction 112 up to a predetermined position ("actuation state"), the platform, 120, washer 604, sealing member 124, and plunger 122 are also moved along the deployment direction 112 by engagement of their respective interconnecting features, as discussed above. Accordingly, the arm 506 compresses the biasing member 118 between the base 502 and the plunger 122, thus applying a load to the biasing member 118.

Figure 7:
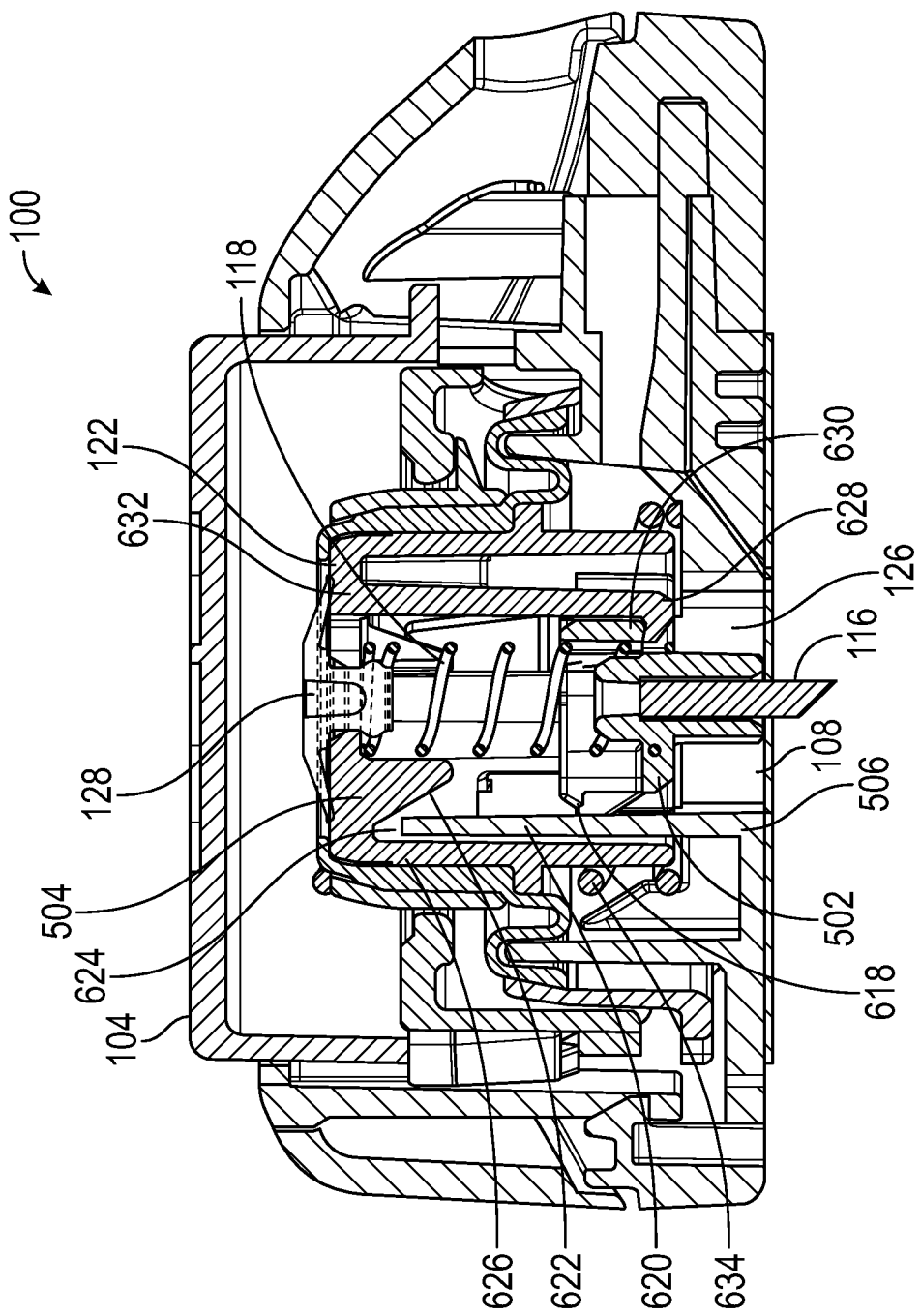
FIG. 7 is a cross-sectional view of the device of FIG. 6A in a deployment state.
Figure 8:
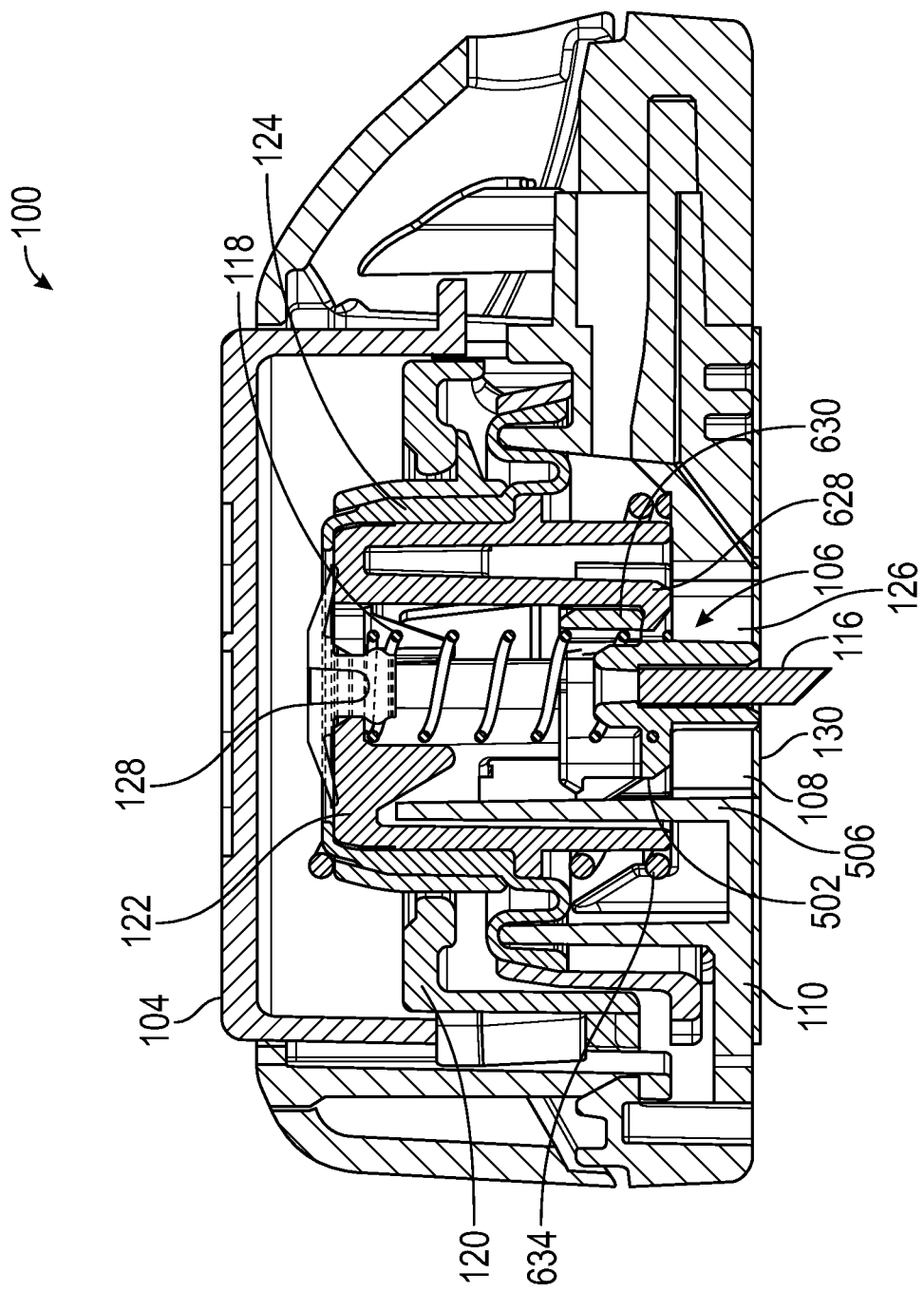
FIG. 8 is a cross-sectional view of the device of FIG. 6A in a peak deployment state.

FIG. 7 is a cross-sectional view of the device 100 when the actuator 104 is moved beyond the predetermined position ("deployment state"), and FIG. 8 is a cross-sectional view of the device 100 when the actuator 104 is at the maximum position along the deployment direction 112 ("peak deployment state"). As the actuator 104 moves beyond the predetermined position, the plunger 122 moves toward the arm 506 until the end portion 620 of the arm 506 contacts at least one projection 504 within the plunger 122. The base 502 can include a notch formed in the hook feature 618 to permit contact between the end portion 620 of the arm 506 and the projection 504. The projection 504 includes an inclined surface 622 that contacts and displaces the arm 506 outward from the hook feature 618 so that the arm 506 moves from the flexed configuration to the released configuration. In the released configuration, the arm 506 disengages from the base 502 and deflects outward into a channel 624 formed between the projection 504 and a sidewall 626 of the plunger 122.

Once the arm 506 disengages the base 502, the load on the biasing member 118 is released (e.g., the stored energy is released), causing the biasing member 118 to drive the base 502 and the skin-piercing feature 116 toward the opening 108. The plunger 122 can optionally include a latch portion 628 to restrict the movement of the skin-piercing feature 116 along the deployment direction 112. In some embodiments, the latch portion engages a complementary stop feature 630 on the base 502 to stop the movement of the base 502 and skin-piercing feature 116 along the deployment direction 112. The latch portion 628 can be positioned away from the upper portion 632 of the plunger 122, with the distance from the upper portion 632 and the latch portion 628 being configured to permit the skin-piercing feature 116 to attain a desired penetration velocity. For example, the distance can be at least about 1 mm, 2 mm, 3 mm, 4 mm, 5 mm, 6 mm, 7 mm, 8 mm, 9 mm, or 10 mm. In some embodiments, the distance can be within a range from about 4 mm to about 8 mm.

Figure 9:
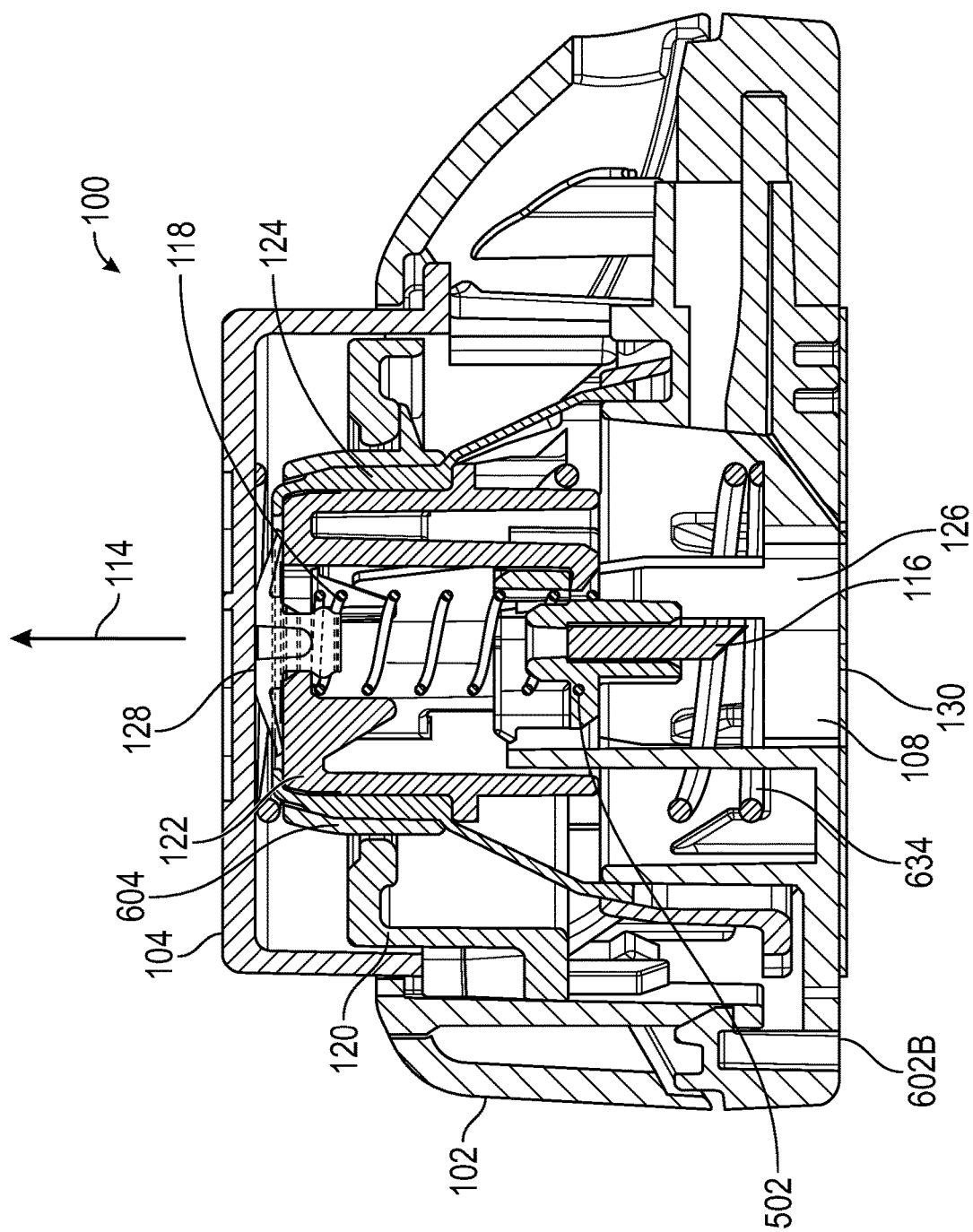
FIG. 9 is a cross-sectional view of the device of FIG. 6A in a retraction state.

FIG. 9 is a cross-sectional view of the device 100 after retraction of the skin-piercing feature 116 ("retraction state"). In some embodiments, the actuation mechanism of the device 100 also automatically retracts the skin-piercing feature 116 after deployment without requiring any additional actuation of the device components by the patient. For example, the device 100 can include a second biasing member 634 (e.g., a spring) configured to bias the skin-piercing feature 116 along the retraction direction 114 away from the opening 108. The second biasing member 634 can have an unloaded state (e.g., an uncompressed state) in which little or no load is placed on the second biasing member 634, and a loaded state (e.g., a compressed state) in which a load is placed on the second biasing member 634. When the load on the second biasing member 634 is released, the second biasing member 634 moves from the loaded state toward the unloaded state, and the movement of the second biasing member 634 toward the unloaded state drives the retraction of the skin-piercing feature 116.

The second biasing member can be coupled between the actuator 104 and the lower housing portion 602B. As shown in FIGS. 7 and 8, movement of the actuator 104 along the deployment direction compresses the second biasing member 634, thus applying a load to the second biasing member 634 causing energy to be stored in the second biasing member 634. When the patient or user stops pushing on the actuator 104, the load on the second biasing member 634 is released, causing the second biasing member 634 to drive the actuator 104 along the retraction direction 114. Movement of the actuator 104 along the retraction direction 114 also moves the platform 120, washer 604, sealing member 124, and plunger 122 along the retraction direction 114 by engagement of their respective interconnecting features, as discussed above. Movement of the plunger 122 along the retraction direction 114 also retracts the biasing member 118, base 502, and skin-piercing feature 116 along the retraction direction 114 away from the opening 108. As the second biasing member 634 moves the platform 120, plunger 122 and sealing member 124 in the retraction direction 114, the volume within the sealing member 124 increases causing a decrease in pressure (e.g., a vacuum) within the volume bounded by the sealing member 124 that draws blood from the patient.

Figure 10:
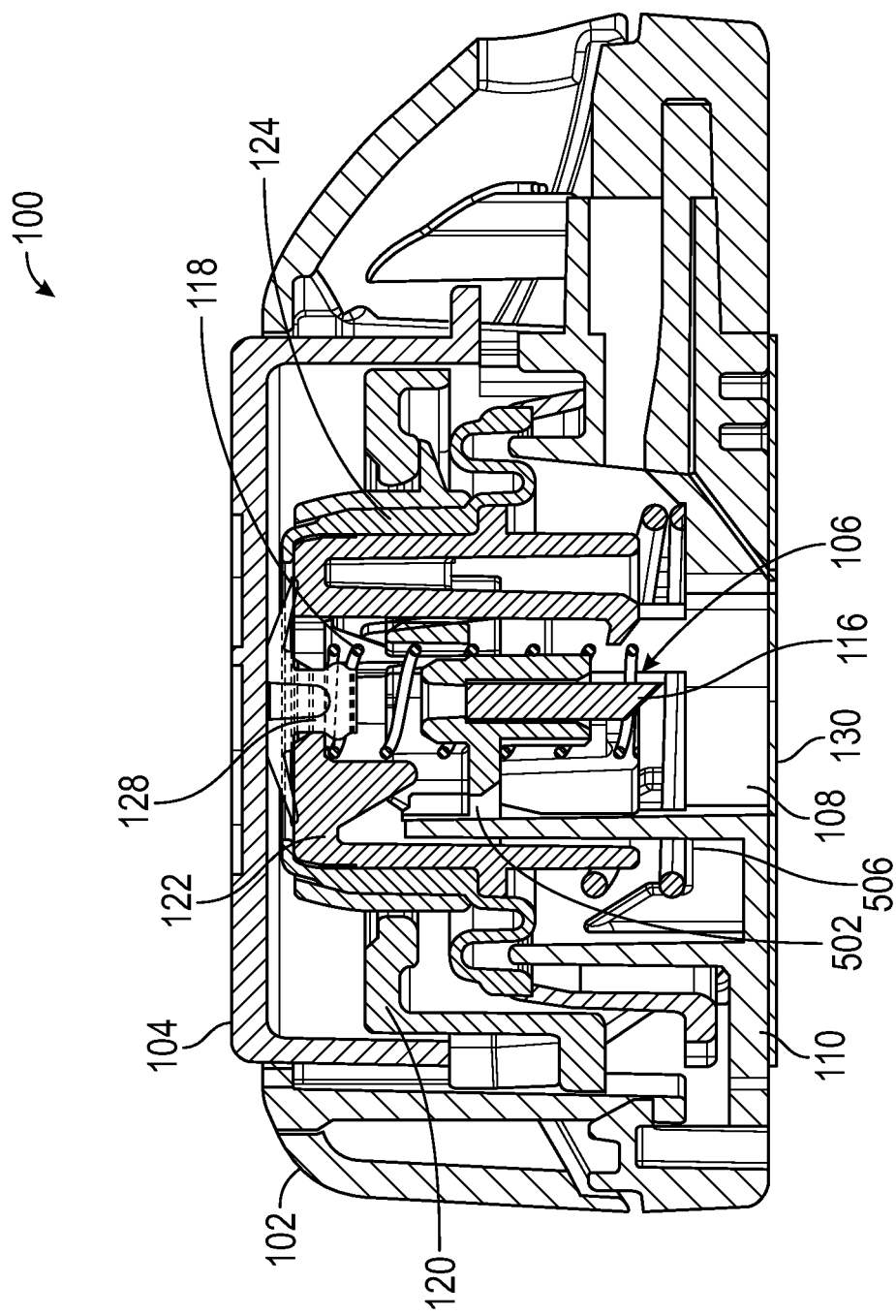
FIG. 10 is a cross-sectional view of the device of FIG. 6A in a re-actuation state.

FIG. 10 is a cross-sectional view of the device 100 when the actuator 104 is moved along the deployment direction 112 after retraction of the skin-piercing feature 116 ("re-actuation state"). The device 100 can include a locking mechanism configured to prevent re-deployment of the skin-piercing feature 116 after the skin-piercing feature 116 has already been retracted. Accordingly, even if the patient presses the actuator 104 again, the skin-piercing feature 116 is retained within the housing 102 and does not deploy. Additional features and implementations of the locking mechanism are described herein with reference to FIGS. 12A-12C.

In some embodiments, the bodily fluid collection devices of the present technology include an actuation mechanism in which the biasing member driving the deployment of the skin-piercing features is partially or fully loaded prior to movement of the actuator ("pre-loaded"). Accordingly, movement of the actuator along the deployment direction simply releases the load on the biasing member, with little or no additional loading applied.

Figure 11A:
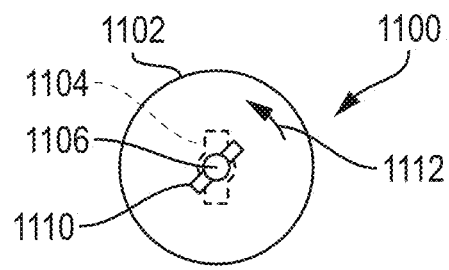
FIGS. 11A-11H are schematic top and cross-sectional illustrations of the operation of a pre-loaded actuation mechanism in accordance with the present technology.
Figure 11E:
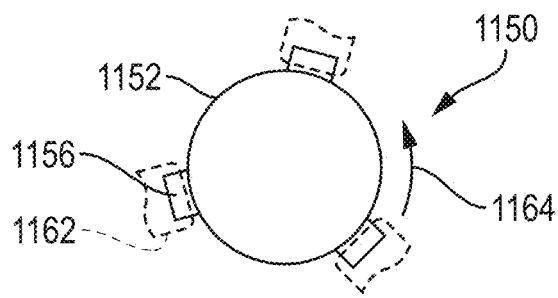
Figure 11B:
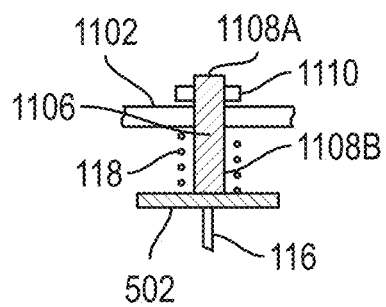
Figure 11F:
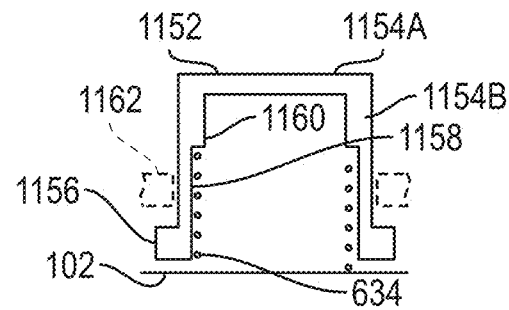
Figure 11C:
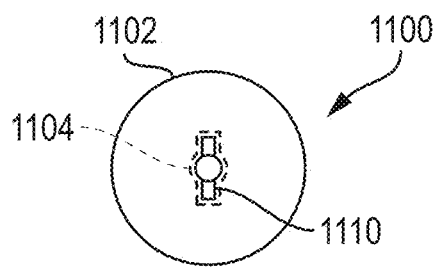
Figure 11G:
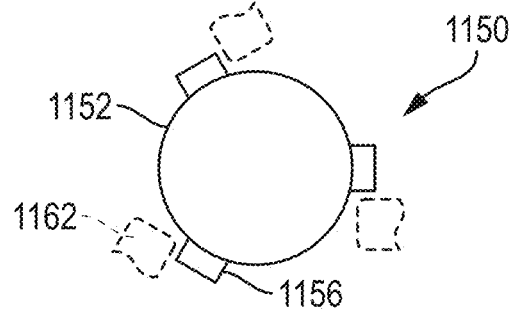
Figure 11D:
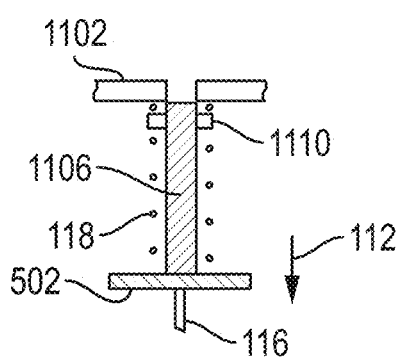
Figure 11H:
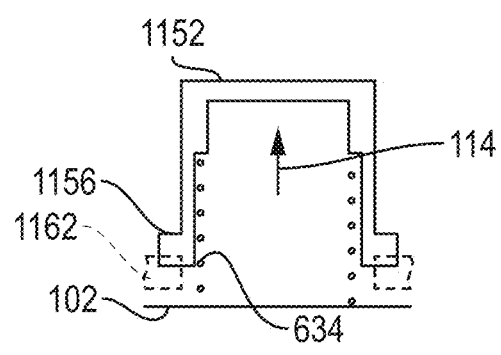

FIGS. 11A-11H are schematic top and cross-sectional illustrations of the operation of a pre-loaded actuation mechanism configured in accordance with an embodiment the present technology. The actuation mechanism includes a deployment assembly 1100 (FIGS. 11A-11D) and a retraction assembly 1150 (FIGS. 11E-11G). As shown in FIGS. 11A (top view) and 11B (cross-sectional view), the deployment assembly 1100 includes a plate 1102, an aperture 1104 in the plate 1102, and a shaft 1106 extending through the aperture 1104. The shaft 1106 includes an upper end portion 1108A and a lower end portion 1108B. The upper end portion 1108A is coupled to at least one stop feature 1110 having a shape complementary to the shape of the aperture 1104. For example, the stop feature 1110 can include one or more tabs protruding radially outward from the shaft 1106, and the aperture 1104 can include one or more recesses shaped to receive the one more tabs. The lower end portion 1108B is coupled to the base 502 carrying the skin-piercing feature 116. The biasing member 118 is positioned at least partially around the shaft 1106 between the lower surface of the plate 1102 and the upper surface of the base 502.

As shown in FIGS. 11A and 11B, prior to actuation of the bodily fluid collection device, the stop feature 1110 is oriented on the upper surface of the plate 1102 such that the stop feature 1110 is not aligned with the aperture 1104. For example, the stop feature 1110 can be rotated relative to the aperture 1104 such that the protrusions of the stop feature 1110 are not over the corresponding recesses of the aperture 1104, and are instead against the upper surface of the plate 1102. Accordingly, the stop feature 1110 prevents movement of the shaft 1106, base 502, and skin-piercing feature 116 toward the deployment direction. The length of the shaft 1106 can be selected such that the biasing member 118 is held between the base 502 and plate 1102 in at least a partially loaded state. For example, the biasing member 118 can be held at a loaded length that is less than or equal to about 5%, 10%, 15%, 20%, 25%, 30%, 35%, 40%, 45%, 50%, 55%, 60%, 65%, 70%, 75%, or 85% of its unloaded length.

During actuation of the bodily fluid collection device, movement of the actuator along the deployment direction causes a rotational movement of the stop feature 1110, e.g., along a rotational direction 1112. The rotational direction 1112 can be a clockwise direction or a counterclockwise direction. As shown in FIGS. 11C (top view) and 11D (cross-sectional view), the rotational movement brings the stop feature 1110 into alignment with the aperture 1104 such that the stop feature 1110 can pass through the aperture 1104. For example, the stop feature 1110 can be rotated such that the protrusions of the stop feature 1110 are over the corresponding recesses of the aperture 1104. The alignment of the stop feature 1110 with the aperture 1104 releases the load on the biasing member 118. Without the stop feature 1110 restraining the biasing member 118 to its loaded length, the biasing member 118 can extend toward its unloaded length, thus driving the base 502 and skin-piercing feature 116 along the deployment direction 112 toward the patient's skin.

The retraction assembly 1150 can be used in combination with the deployment assembly 1100 to retract the skin-piercing feature 116 after deployment. For example, the retraction assembly 1150 can be around at least a portion of the deployment assembly 1100 and/or the skin-piercing feature 116. As shown in FIGS. 11E (top view) and 11F (cross-sectional view), the retraction assembly 1150 includes a cap 1152 having an outer surface 1154A and an inner surface 1154B. The cap 1152 includes one or more protrusions 1156 extending radially outward from the outer surface 1154A. The second biasing member 634 is received within a groove 1158 formed in the inner surface 1154B of the cap 1152. The second biasing member 634 is coupled between an inner collar 1160 of the cap 1152 and the housing 102 of the device. The retraction assembly 1150 further includes one or more latch features 1162 extending radially inward toward the cap 1152. The latch features 1162 can be on a portion of the device that is stationary relative to the skin-piercing feature 116, such as the housing 102.

As shown in FIGS. 11E and 11F, prior to deployment of the skin-piercing feature 116, the cap 1152 can be oriented such that the protrusions 1156 are aligned with the latch features 1162. The latch features 1162 can engage the protrusions 1156 such that the cap 1152 is held in place relative to the housing 102. The height of the groove 1158 within the cap 1152 can be selected such that the second biasing member 634 is held between the inner collar 1160 and the housing 102 in at least a partially loaded state. For example, the second biasing member 634 can be held at a loaded length that is less than or equal to about 5%, 10%, 15%, 20%, 25%, 30%, 35%, 40%, 45%, 50%, 55%, 60%, 65%, 70%, 75%, or 85% of its unloaded length.

The deployment of the skin-piercing feature causes a rotational movement of the cap 1152, e.g., along a rotational direction 1164. The rotational direction 1164 can be a clockwise direction or a counterclockwise direction. As shown in FIG. 11G (top view) and FIG. 11H (cross-sectional view), the rotational movement brings the latch features 1162 out of alignment with the protrusions 1156, thus releasing the load on the second biasing member 634. The second biasing member 634 can extend toward its unloaded length, thus driving the cap 1152 along the retraction direction 114. The cap 1152 can be mechanically coupled to the skin-piercing feature 116 such that movement of the second biasing member 634 toward its unloaded length moves the skin-piercing feature 116 along the retraction direction 114 away from the patient's skin.

The features of the deployment assembly 1100 and the retraction assembly 1150 can be varied as desired. For example, various numbers, sizes, and/or shapes of the stop feature 1110 and/or aperture 1104 can be used. In some embodiments, the stop feature 1110 includes one, two, three, four, five, or more tabs; and the aperture 1104 includes one, two, three, four, five, or more corresponding recesses. As another example, the number, size, and/or shape of the protrusions 1156 and/or latch features 1162 can be varied as desired. For example, the retraction assembly 1150 can include one, two, three, four, five, or more protrusions; and one, two, three, four, five, or more latch features.

The bodily fluid collection devices of the present technology can include a locking mechanism configured to prevent re-deployment of a skin-piercing feature after the skin-piercing feature has been deployed and retracted into the device. The locking mechanism is expected to improve safety by making the device single-use only, thus reducing the risk of injury or accidental reuse of a contaminated device. In some embodiments, the locking mechanism includes a switchable feature that is movable between a pre-retraction configuration and a post-retraction configuration. The switchable feature can initially be in the pre-retraction configuration, and can be moved into the post-retraction configuration with the retraction of the skin-piercing feature. In the post-retraction configuration, the switchable feature can constrain the movement of one or more device components (e.g., the actuator, plunger, skin-piercing assembly) to prevent the skin-piercing feature from being re-deployed even if the actuator is moved along the deployment direction. For example, the switchable feature can constrain the one or more device components to move along a movement path that is different from a pre-retraction movement path and does not permit the skin-piercing feature to re-deploy.

Figure 12A:
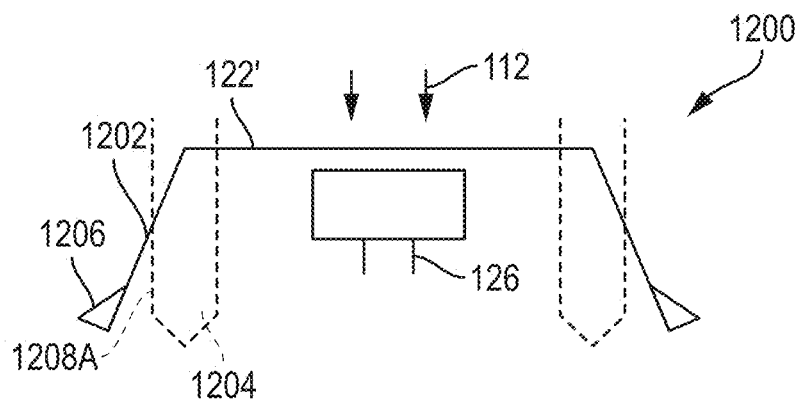
FIGS. 12A-12C are schematic cross-sectional illustrations of the operation of a locking mechanism configured in accordance with an embodiment of the present technology.
Figure 12B:
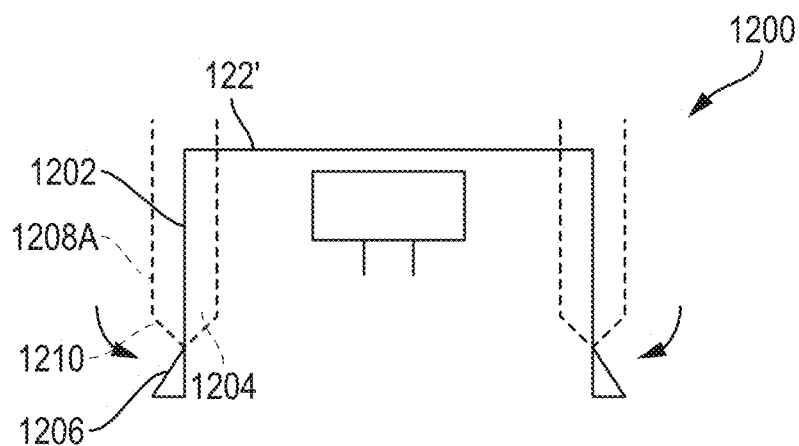
Figure 12C:
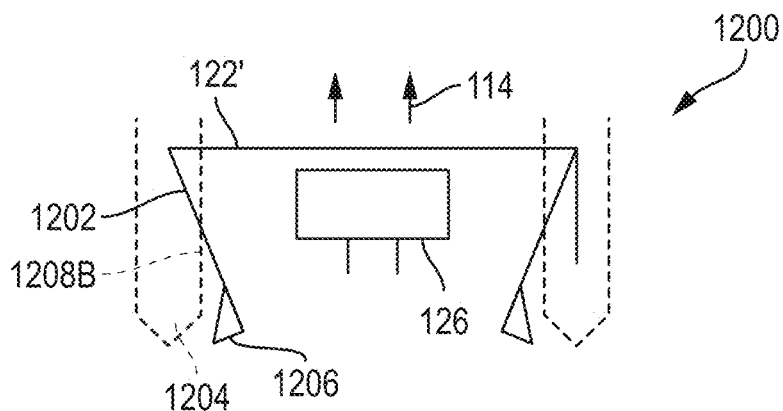

FIGS. 12A-12C are schematic cross-sectional illustrations of the operation of a locking mechanism 1200 configured in accordance with an embodiment the present technology. The locking mechanism 1200 can be incorporated into any embodiment of the bodily fluid collection devices disclosed herein. For example, the locking mechanism 1200 can be incorporated into the device 100 of FIGS. 6A-10. As another example, the locking mechanism 1200 can be used in combination with the actuation mechanism of FIGS. 11A-11H.

The locking mechanism 1200 includes one or more switchable features 1202 and one or more guide features 1204. The switchable features 1202 are on a component that is mechanically coupled to the skin-piercing feature 116, such as a ring 122' or the actuator 104 (not shown). The guide features 1204 can be on a component of the device that remains stationary relative to the skin-piercing feature 116, such as the housing 102 (not shown).

The switchable features 1202 are movable between a pre-retraction configuration and a post-retraction configuration. As shown in FIG. 12A, prior to movement of the actuator along the deployment direction 112, the switchable features 1202 are initially in the pre-retraction configuration with their contact portions 1206 along a first surface 1208A of the guide features 1204. For example, in the pre-retraction configuration, the switchable features 1202 can be bent radially outward with the contact portions 1206 along an outer surface of the guide features 1204. The first surface 1208A applies a load to the contact portions 1206 to maintain the switchable features 1202 in the pre-retraction configuration and prevent the switchable feature 1202 from reverting to the post-retraction configuration.

As shown in FIG. 12B, as the ring 122' moves along the deployment direction 112 during deployment of the skin-piercing feature 116, the contact portions 1206 of the switchable features 1202 slide along the deployment direction 112 against the first surface 1208A until they reach the end portions 1210 of the guide features 1204, releasing the load on the contact portions 1206 and allowing the switchable features 1202 to revert to the post-retraction configuration. The movement of the switchable features 1202 to the post-retraction configuration can include linear, radial, and/or rotational movements. In some embodiments, the movement of the switchable features 1202 only includes linear and/or radial movements and does not involve any rotational movements. For example, in the post-retraction configuration, the switchable features 1202 can be bent radially inward.

As shown in FIG. 12C, when the ring 122' moves along the retraction direction 114 during the retraction of the skin-piercing feature 116, the contact portions 1206 of the switchable features 1202 slide along the retraction direction 114 against a second surface 1208B of the guide features 1204. The second surface 1208B can be an inner surface of the guide features 1204. The switchable features 1202 can be biased toward the post-retraction configuration, such that the switchable features 1202 do not revert to the pre-retraction configuration even if the ring 122' subsequently moves along the deployment direction 112. The post-retraction configuration of the switchable features 1202 can constrain the movement of the ring 122' to a movement path that prevents the skin-piercing feature 116 from being re-deployed. For example, the ring 122' can be disengaged from one or more device components (e.g., actuator, platform, collar, skin-piercing assembly) involved in deployment of the skin-piercing feature 116 while the ring 122' moves along the movement path.

The features of the locking mechanism 1200 can be varied as desired. For example, although FIGS. 12A-12C illustrate a mechanism 1200 with two switchable features and two guide features, alternative embodiments may include any suitable number of switchable features and guide features. In some embodiments, the mechanism 1200 can include one, two, three, four, five, or more switchable features; and one, two, three, four, five, or more guide features. The positioning of the switchable features and guide features can also be varied. For instance, the switchable features 1202 can be on the actuator, platform, collar, plunger, and/or skin-piercing assembly. The positioning of the switchable features 1202 and the guide features 1204 can also be reversed, such that the switchable features 1202 are on a component that remain stationary relative to the skin-piercing feature 116, and the guide features 1204 are on a component that moves along with the skin-piercing feature 116. Additionally, although FIGS. 12A-12C illustrate the contact portions 1206 of the switchable features 1202 being bent outward in the pre-retraction configuration and bent inward in the post-retraction configuration, in alternative implementations, the contact portions 1206 can be bent inward in the pre-retraction configuration and bent outward in the post-retraction configuration.

III. VACUUM MECHANISM

The bodily fluid collection devices of the present technology can include a vacuum mechanism configured to apply a vacuum to the patient's skin to facilitate withdrawal of larger volumes of bodily fluid. In some embodiments, the vacuum deforms the skin into a curved shape that opens the capillaries within the skin to increase the local flow of bodily fluid, and also maintains the incision in an opened configuration to promote withdrawal of bodily fluid into the device. For example, the vacuum can be applied by expanding the volume within a flexible membrane, such as the sealing member 124 described above, as opposed to actively drawing air out of a rigid cup (e.g., withdrawing air from a suction cup.) The timing of vacuum application relative to the other steps in the operation of the bodily fluid collection device can be varied as desired. For example, the vacuum can be applied prior to, concurrently with, and/or after the deployment of the skin-piercing feature to pierce the skin. As another example, the vacuum can be applied prior to, concurrently with, and/or after the retraction of the skin-piercing feature away from the skin. The vacuum mechanisms of the present technology can be used in combination with any of the actuation mechanisms disclosed herein, such as the actuation mechanisms described with reference to FIGS. 4-12C.

Figure 13A:
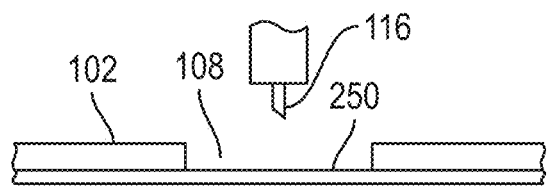
FIGS. 13A-13D are schematic cross-sectional illustrations of a vacuum being applied to a patient's skin in accordance with an embodiment of the present technology.
Figure 13B:
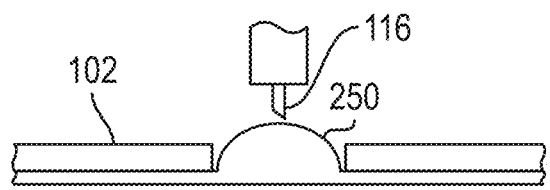
Figure 13C:
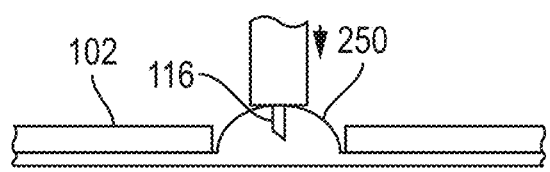
Figure 13D:
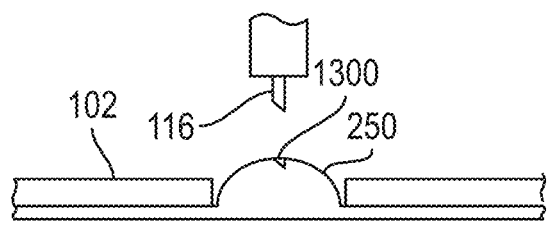

FIGS. 13A-13D, for example, are schematic cross-sectional illustrations of a vacuum being applied to a patient's skin 250 configured in accordance with an embodiment the present technology. The device is initially applied to the patient's body with the housing 102 and opening 108 against the skin 250 (FIG. 13A). A vacuum is applied to the skin 250 to pull at least a portion of the skin 250 into a curved shape (FIG. 13B). The skin 250 can be pulled at least partially into the device, such as being pulled at least partially through the opening 108 and into the interior of the housing. While the skin 250 is under vacuum, a skin-piercing feature 116 is deployed and pierces the skin 250 to create an incision 1300 (FIG. 13C). The skin-piercing feature 116 can be then retracted to permit bodily fluid to flow from the incision 1300 into the housing 102 (FIG. 13D).

Figure 14A:
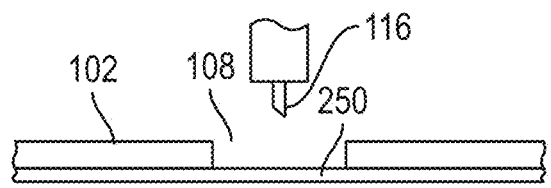
FIGS. 14A-14C are schematic cross-sectional illustrations of a vacuum being applied to a patient's a patient's skin in accordance with an embodiment of the present technology.
Figure 14B:
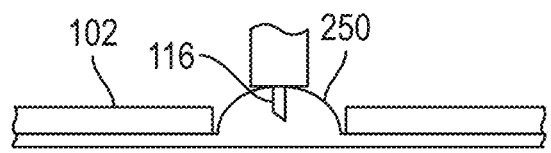
Figure 14C:
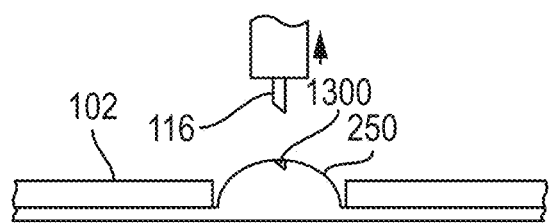

FIGS. 14A-14C are schematic cross-sectional illustrations of a vacuum being applied to a patient's skin 250 configured in accordance with an embodiment the present technology. The device is initially applied to the patient's body with the housing 102 and opening 108 against the skin 250 (FIG. 14A). A vacuum is applied to the skin 250 to pull at least a portion of the skin 250 into a curved shape (FIG. 14B). The skin 250 can be pulled at least partially into the device, such as through the opening 108 and into the interior of the housing 102, and the skin-piercing feature 116 can pierce the skin 250 to create an incision 1300. In some embodiments, the skin-piercing feature 116 is held stationary as the skin 250 is pulled into contact with the skin-piercing feature 116. Alternatively, the skin-piercing feature 116 can be concurrently deployed toward the skin 250 as the vacuum is applied. The skin-piercing feature 116 can then be retracted to permit bodily fluid to flow from the incision 1300 into the housing 102 (FIG. 14C).

In some embodiments, the bodily fluid collection device does not include a pre-existing vacuum source. Instead, the device includes a vacuum mechanism that generates a vacuum along with the deployment and/or retraction of the skin-piercing feature ("dynamically-generated vacuum"). For example, the vacuum mechanism can include a lumen that is initially at or near atmospheric pressure (e.g., gauge pressure is about 0 kPa). When the device is actuated (e.g., during deployment and/or retraction of skin-piercing feature), the vacuum mechanism can lower the pressure within the lumen to less than atmospheric pressure by expanding the volume of the lumen as opposed to withdrawing gas from the lumen, thereby creating a vacuum within the lumen. For example, the lumen can be at a gauge pressure less than or equal to about −10 kPa, −15 kPa, −20 kPa, −25 kPa, −30 kPa, −35 kPa, −40 kPa, −45 kPa, −50 kPa, −55 kPa, or −60 kPa. The lumen can be in fluidic connection with the skin, or a device component that contacts the skin (e.g., the flexible membrane), to apply the vacuum directly or indirectly to the skin.

In some embodiments, the lumen is mechanically coupled to one or more movable components of the bodily fluid collection device, such that movement of the component along the deployment direction decreases the volume of the lumen, and movement of the component along the retraction increases the volume of the lumen. For example, the lumen can be at least partially formed from a sealing member (e.g., a flexible membrane) that is deformable to increase or decrease the volume of the lumen. In another example, the lumen can be formed from 2 solid cylinders in contact that are able to slide one relative to the other. The vacuum mechanism can further include at least one valve fluidically connected to the lumen to control air flow into and out of the lumen. The valve can be a one-way valve (e.g., a check valve) that permits air to escape from within the lumen as the lumen volume decreases, but prevents air from entering the lumen as the lumen volume increases to dynamically generate a vacuum within the lumen. In other embodiments, the valve can be mechanically shut as the actuation mechanism reaches a predetermined position prior or at the same time as full actuation.

Figure 15A:
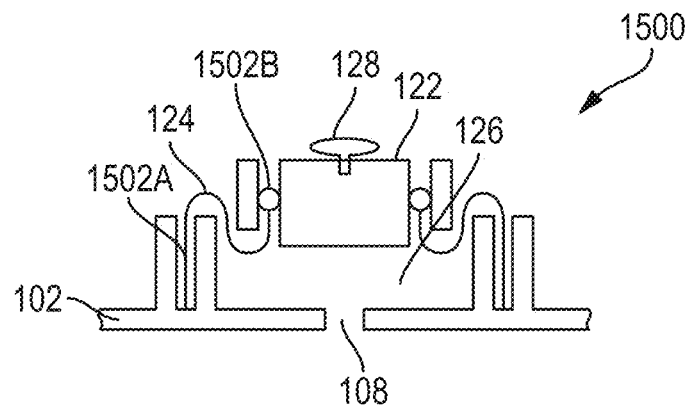
FIGS. 15A-15C are schematic cross-sectional illustrations of the operation of a dynamically-generated vacuum mechanism in accordance with an embodiment of the present technology.
Figure 15B:
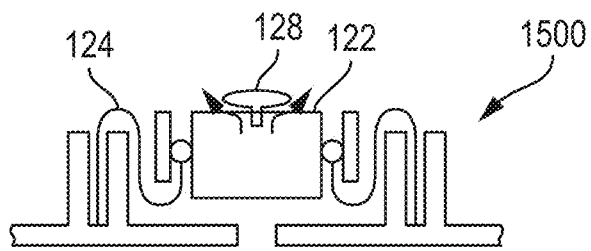
Figure 15C:
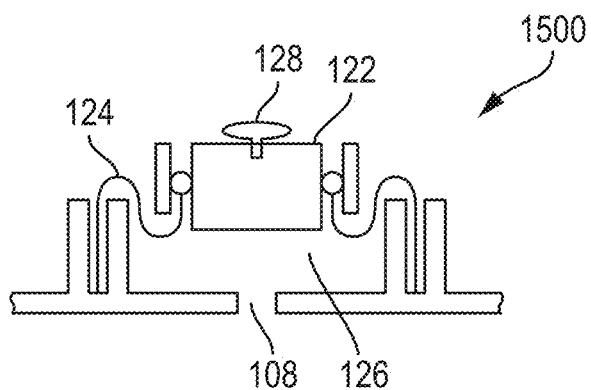

FIGS. 15A-15C are schematic cross-sectional illustrations of the operation of a dynamically-generated vacuum mechanism 1500 configured in accordance with an embodiment the present technology. The vacuum mechanism 1500 includes the sealing member 124, which is at least partially over the opening 108 in the housing 102 of the bodily fluid collection device. The sealing member 124 has an outer portion 1502A and an inner portion 1502B. The outer portion 1502A of the sealing member 124 is connected to the housing 102, and the inner portion 1502B of the sealing member 124 is connected to the plunger 122, thus a forming a lumen 126 in fluidic connection with the opening 108. The plunger 122 includes the valve 128 (e.g., an umbrella valve) in fluidic connection with the lumen 126. The plunger 122 can be connected to the skin-piercing assembly 106 (not shown), as described herein.

The device is initially applied to the patient's body with the opening 108 against the patient's skin, such that the lumen 126 is sealed between the sealing member 124, plunger 122, housing 102, and the skin. Prior to movement of the actuator of the device (FIG. 15A), the pressure within the lumen 126 is at or near atmospheric pressure, and the valve 128 is closed. When the actuator is moved along the deployment direction (e.g., to deploy the skin-piercing feature), the plunger 122 also moves along the deployment direction toward the opening 108, thus reducing the volume of the lumen 126 (FIG. 15B). The reduction in volume produces a corresponding increase in the pressure within the lumen 126, causing the valve 128 to open and permit air to escape from within the lumen 126. For example, the valve 128 can be configured to open when the gauge pressure within the lumen is greater than or equal to about 0.1 kPa, 0.2 kPa, 0.3 kPa, 0.4 kPa, 0.5 kPa, 0.6 kPa, 0.7 kPa, 0.8 kPa, 0.9 kPa, 1.0 kPa, 1.5 kPa, 2 kPa, 2.5 kPa, 3.0 kPa, or 4 kPa.

When the plunger 122 moves along the retraction direction away from the opening (e.g., when the skin-piercing feature is retracted), the volume of the lumen 126 increases (FIG. 15C). The valve 128 prevents air from entering the lumen 126 as the volume increases, thus producing a corresponding decrease in pressure within the lumen 126. The decreased pressure produces a vacuum that pulls the patient's skin at least partially into the device (e.g., pulls the skin at least partially through the opening 108 and into the lumen 126).

Referring back to FIGS. 6A-9, the bodily fluid collection device 100 can include a dynamically-generated vacuum mechanism configured in accordance with an embodiment the present technology. In some embodiments, the vacuum mechanism includes the sealing member 124. The sealing member 124 is coupled to the housing 102 and plunger 122 to define the lumen 126. The sealing member 124 can be movable between a collapsed configuration in which the volume of the lumen 126 is decreased, and an extended configuration in which the volume of the lumen 126 is increased. In some embodiments, the sealing member 124 is mechanically coupled to the plunger 122 so that the movement of the plunger 122 also moves the sealing member 124 between the collapsed and extended configurations.

The sealing member 124, housing 102, and plunger 122 can be connected to each other via airtight connections to allow for creation of a low-pressure region (e.g., a vacuum) within the lumen 126. In some embodiments, the outer portion 1502A of the sealing member 124 is coupled between the housing 102 and a retaining element 640. The retaining element 640 can be a ring-like structure that compresses the outer portion 1502A against a cylindrical portion 642 of the housing 102 to create an airtight connection between the sealing member 124 and the housing 102. The inner portion 1502B of the sealing member 124 is connected to the upper surface of the plunger 122. The valve 128 (e.g., an umbrella valve) extends through the upper surface of the plunger 122 to control air flow into and out of the lumen 126.

Prior to movement of the actuator of the device (FIG. 6A), the pressure within the lumen 126 is at or near atmospheric pressure, and the valve 128 is closed. During deployment of the skin-piercing feature 116 (FIGS. 7 and 8), the plunger 122 moves along the deployment direction 112, thus moving the sealing member 124 into the collapsed configuration and reducing the volume of the lumen 126. The reduction in volume produces a corresponding increase in the pressure within the lumen 126, causing the valve 128 to open and permit air to escape from within the lumen 126.

During retraction of the skin-piercing feature 116 (FIG. 9), the plunger 122 moves along the retraction direction 114, thus pulling the sealing member 124 into the extended configuration and increasing the volume of the lumen 126. The valve 128 prevents air from entering the lumen 126 as the volume increases, thus producing a corresponding decrease in pressure within the lumen 126. The decreased pressure produces a vacuum that pulls the patient's skin at least partially through the opening 108 and into the lumen 126.

Figure 16A:
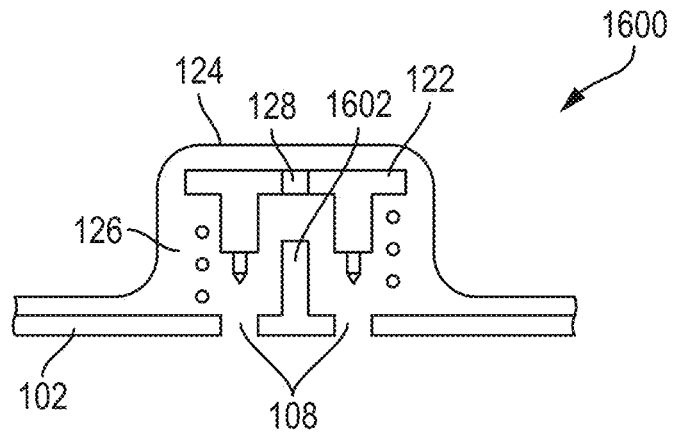
FIGS. 16A-16C are schematic cross-sectional illustrations of the operation of another dynamically-generated vacuum mechanism in accordance with an embodiment of the present technology.
Figure 16B:
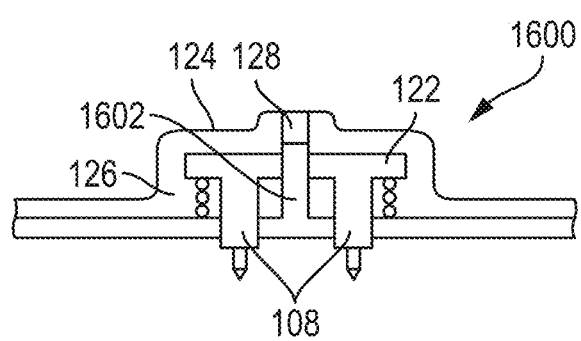
Figure 16C:
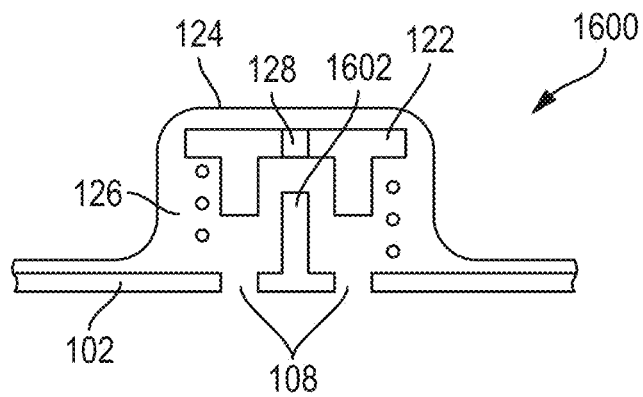

FIGS. 16A-16C are schematic cross-sectional illustrations of the operation of another dynamically-generated vacuum mechanism 1600 configured in accordance with an embodiment the present technology. The vacuum mechanism 1600 includes the sealing member 124 connected to the housing 102 and the plunger 122 to form the lumen 126. The lumen 126 is in fluidic connection with one or more openings 108 in the housing 102. The plunger 122 includes the valve 128 in fluidic connection with the lumen 126. The housing 102 includes a prong 1602 extending into the lumen 126 toward the valve 128. The valve 128 can be a mechanically actuated valve that is opened and/or closed by engagement with the prong 1602.

The device is initially applied to the patient's body with the opening 108 against the patient's skin, such that the lumen 126 is sealed between the sealing member 124, plunger 122, housing 102, and the skin. Prior to movement of the actuator of the device (FIG. 16A), the pressure within the lumen 126 is at or near atmospheric pressure, and the valve 128 is closed. When the actuator is moved along the deployment direction (e.g., to deploy the skin-piercing feature), the plunger 122 also moves along the deployment direction toward the opening 108, thus bringing the prong 1602 in contact with the valve 128 (FIG. 16B). The prong 1602 can engage and open the valve 128 to permit air to escape from within the lumen 126.

When the plunger 122 moves along the retraction direction away from the opening (e.g., when the skin-piercing feature is retracted), the prong 1602 is disengaged from the valve 128 (FIG. 16C). The prong 1602 can close the valve 128 as it disengages from the valve 128, thus preventing air from entering the lumen 126. Accordingly, as the volume of the lumen 126 increases, the pressure within the lumen 126 decreases, producing a vacuum that pulls the patient's skin at least partially through the openings 108 and into the lumen 126.

Figure 17A:
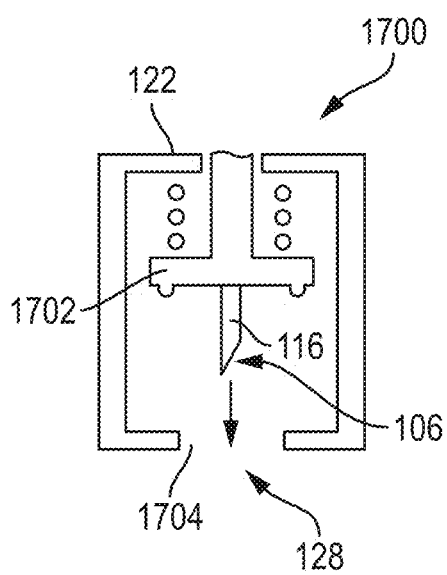
FIGS. 17A and 17B are schematic cross-sectional illustrations of the operation of a dynamically-generated vacuum mechanism integrated into the skin-piercing assembly in accordance with an embodiment of the present technology.
Figure 17B:
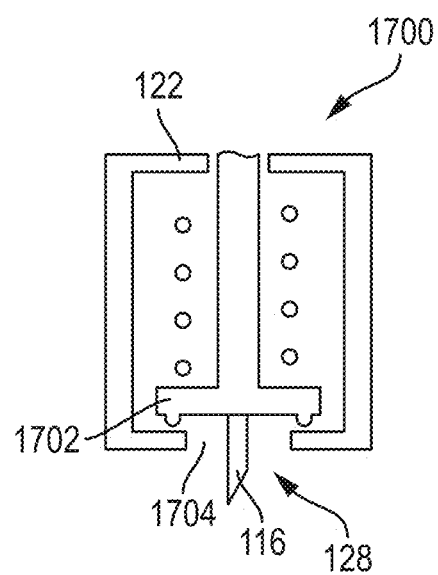

FIGS. 17A and 17B are schematic cross-sectional illustrations of the operation of a dynamically-generated vacuum mechanism 1700 integrated into the skin-piercing assembly 106 configured in accordance with an embodiment the present technology. In the mechanism 1700, the skin-piercing assembly 106 itself forms part of the valve 128. For example, the valve 128 can include a valve member 1702 (e.g., a disk, seal, or gasket) and an opening 1704 that connects to the vacuum lumen (not shown). The valve member 1702 can be made of rubber or a similar material that forms an airtight seal when placed against the opening 1704. The valve member 1702 can be on the skin-piercing assembly 106, such as near the skin-piercing feature 116. The skin-piercing assembly 106 can be at least partially within the plunger 122, and the opening 1704 can be formed in the plunger 122. The valve 128 can be opened when the valve member 1702 is away from the opening 1704 (e.g., prior to deployment of the skin-piercing feature 116) (FIG. 17A). The valve 128 can be closed when the skin-piercing feature and the valve member 1702 is against the opening 1704 (e.g., after deployment of the skin-piercing feature 116) (FIG. 17B).

Figure 18A:
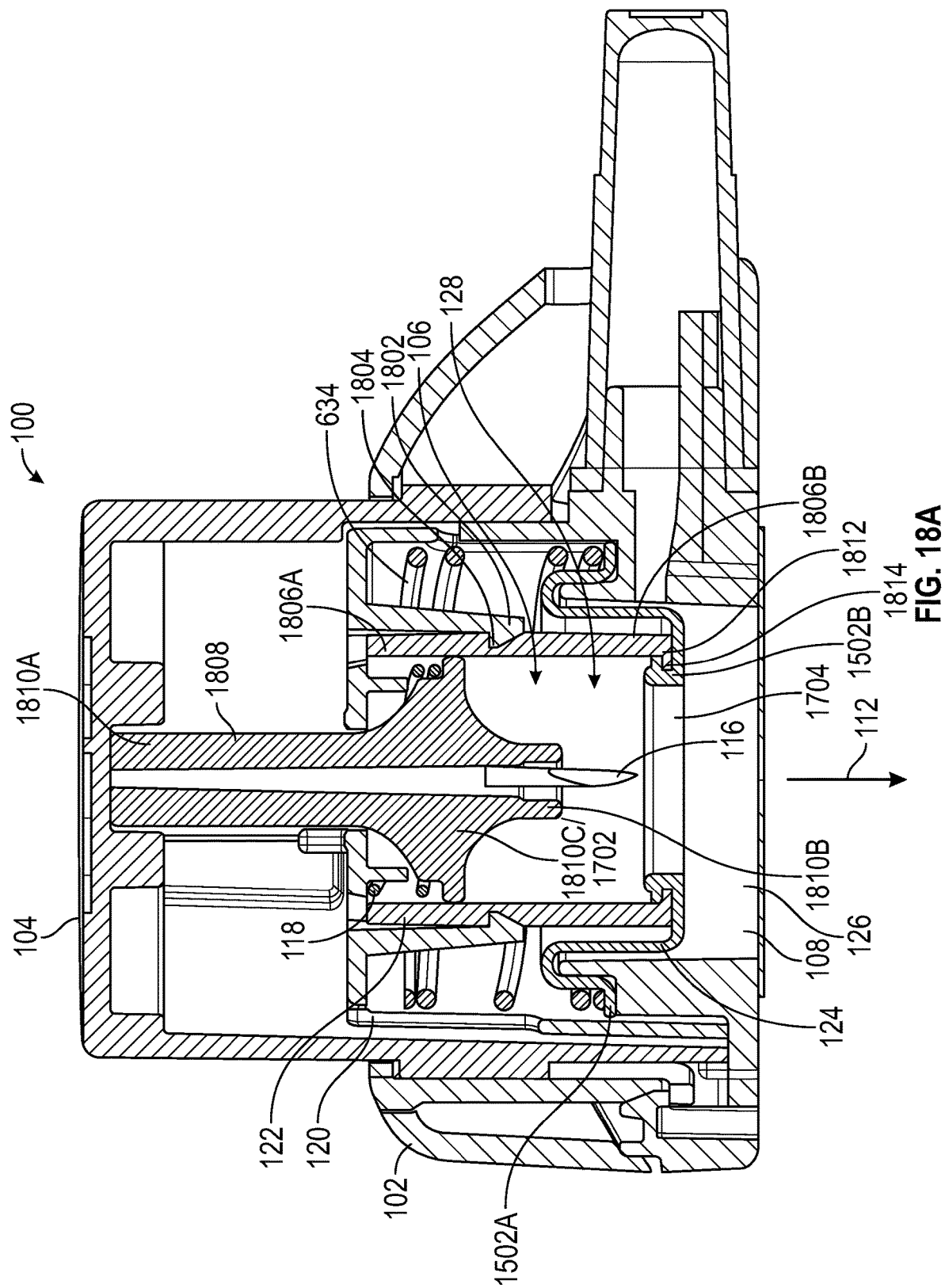
FIGS. 18A and 18B are cross-sectional views of a bodily fluid collection device having a dynamically-generated vacuum mechanism integrated into the skin-piercing assembly and configured in accordance with an embodiment of the present technology.
Figure 18B:
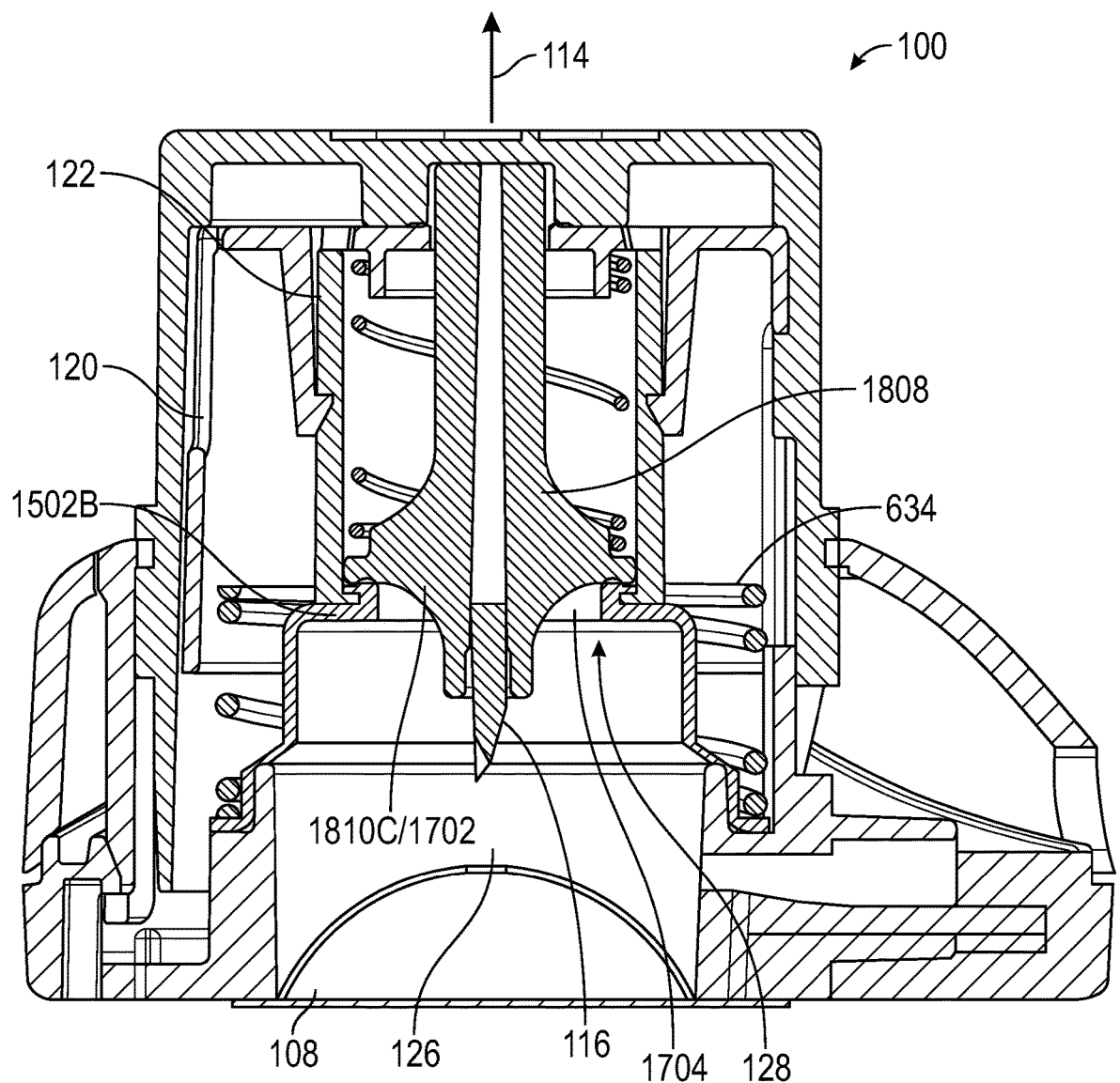

FIGS. 18A and 18B are cross-sectional views of a bodily fluid collection device 100 having a dynamically-generated vacuum mechanism integrated into the skin-piercing assembly 106 configured in accordance with an embodiment the present technology. The device 100 includes the housing 102, the actuator 104, and the skin-piercing assembly 106. The housing 102 includes the upper housing portion 602A and the lower housing portion 602B. The upper housing portion 602A is shaped to receive the actuator 104. The lower housing portion 602B includes the bottom surface 110 having the opening 108.

The actuator 104 is at least partially within the upper housing portion 602A of the device 100. The actuator 104 is mechanically coupled to the skin-piercing assembly 106 via one or more internal device components, such as the platform 120, plunger 122, and/or sealing member 124. In some embodiments, the actuator 104 is positioned around at least a portion of the platform 120, and the platform 120 is positioned around at least a portion of the plunger 122 and/or sealing member 124. The actuator 104, platform 120, plunger 122, and/or sealing member 124 can be concentrically positioned, such that the longitudinal axes of these components are aligned.

The actuator 104, platform 120, plunger 122, and sealing member 124 can be coupled to each other using any suitable combination of complementary interconnecting features (e.g., notches, grooves, projections, tabs, and the like). For example, the platform 120 can include one or more hook features 1802 that engage one or more complementary notch features 1804 on the plunger 122, such that movement of the platform 120 along the deployment direction 112 also moves the plunger 122 along the deployment direction. The plunger 122 can be a hollow structure with an upper portion 1806A and a lower portion 1806B. The upper portion 1806A can be coupled to the platform 120, and the lower portion 1806B can be coupled to the sealing member 124.

The skin-piercing assembly 106 includes a shaft 1808 at least partially within the plunger 122. The shaft 1808 has an upper end portion 1810A, a lower end portion 1810B, and a flared portion 1810C. The longitudinal axis of the shaft 1808 can be aligned with the deployment direction 112 such that the upper end portion 1810A is away from the opening 108 and the lower end portion 1810B is toward the opening 108. The flared portion 1810C can be between the upper end portion 1810A and the lower end portion 1810B. The flared portion 1810C can have a larger diameter than the upper end portion 1810A and the lower end portion 1810B. The shaft 1808 is movable relative to the plunger 122 along the deployment direction 112 and the retraction direction 114.

The skin-piercing assembly 106 further includes the skin-piercing feature 116 and the biasing member 118. The skin-piercing feature 116 is coupled to the lower end portion 1810B of the shaft 1808. The biasing member 118 is positioned within the plunger 122 around at least a portion of the shaft 1808. In some embodiments, the biasing member 118 is coupled between the flared portion 1806C of the shaft 1808 and the platform 120, such that the biasing member 118 drives the shaft 1808 downward relative to the plunger 122 during deployment of the skin-piercing feature 116.

The sealing member 124 includes the outer portion 1502A and the inner portion 1502B. The outer portion 1502A is connected to the housing 102 and the inner portion 1502B is connected to the plunger 122, thus forming a lumen 126 in fluidic connection with the opening 108. In some embodiments, the lower portion 1806B of the plunger 122 includes a collar 1812 that is received within a corresponding groove 1814 in the inner portion 1502B of the sealing member 124 to form an airtight seal between the plunger 122 and sealing member 124.

In some embodiments, the skin-piercing assembly 106, plunger 122, and sealing member 124 collectively form a valve 128 fluidically connected to the lumen 126. The lower portion 1806B of the plunger 122 and the inner portion 1502B of the sealing member 124 can be open so as to form the opening 1704 of the valve 128. The flared portion 1810C of the shaft 1808 of the skin-piercing assembly 106 can serve as the valve member 1702 of the valve 128. The valve 128 can be opened when the valve member 1702 is away from the opening 1704 (e.g., when the flared portion 1810C of the shaft 1808 is toward the upper portion 1806A of the plunger 122) (FIG. 18A). The valve 128 can be closed when the valve member 1702 is against the opening 1704 (e.g., when the flared portion 1810C of the shaft 1808 is toward the lower portion 1806B of the plunger 122) (FIG. 18B).

The device is initially applied to the patient's body with the opening 108 against the patient's skin, such that the lumen 126 is sealed between the sealing member 124, plunger 122, housing 102, and the skin. Prior to deployment of the skin-piercing feature 116 (FIG. 18A), the pressure within the lumen 126 is at or near atmospheric pressure. The valve 128 is in the open state, with the valve member 1702 is away from the opening 1704. During deployment, the biasing member 118 drives the shaft 1808 along the deployment direction 112 so that the skin-piercing feature 116 is moved toward the opening 108. The movement of the shaft 1808 also drives the valve member 1702 against the opening 1704, thus closing the valve 128.

During retraction of the skin-piercing feature 116, the second biasing member 634 is between the platform 120 and the housing 102, and drives the platform 120 along the retraction direction 114. The movement of the platform 120 produces a corresponding movement of the plunger 122 along the retraction direction 114. The movement of the plunger 122 pulls the inner portion 1502B of the sealing member 124 along the retraction direction 114, resulting in an increase in volume of the lumen 126. The shaft 1808 maintains its deployed position relative to the plunger 122 such that the valve 128 remains closed, preventing air from entering the lumen 126 (FIG. 18B). Accordingly, the pressure within the lumen 126 decreases, producing a vacuum that pulls the patient's skin at least partially through the opening 108 and into the lumen 126.

IV. SKIN INTERFACE

In some embodiments, the bodily fluid collection devices of the present technology include a skin interface that interacts with the patient's skin and/or bodily fluid to enhance withdrawal of the bodily fluid into the device. For example, the skin interface can control a curvature of the skin pulled into the device (e.g., via the vacuum mechanisms described herein with reference to FIGS. 13A-18B) to maintain the incision in an open position that facilitates flow of bodily fluid from the skin. Other purposes of the skin interface is to present a controlled surface on which to collect and direct the flowing bodily fluids to prevent fouling or contamination from the surface of the skin and maintain the skin of the user cleaner. In some embodiments, the skin interface is configured to facilitate rapid removal of bodily fluid from the skin to reduce coagulation of the bodily fluid and/or reduce activation of components within the bodily fluid. For example, in embodiments where the bodily fluid is blood, the skin interface can be configured to quickly remove blood from the skin to reduce blood coagulation and/or platelet activation.

Figure 19A:
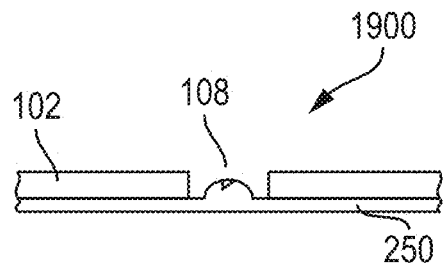
FIGS. 19A-19E are schematic cross-sectional illustrations of skin interfaces to control skin curvature in accordance with embodiments of the present technology.

FIGS. 19A-19E are schematic cross-sectional illustrations of skin interfaces to control skin curvature configured in accordance with an embodiment the present technology. FIG. 19A illustrates a skin interface 1900 including the housing 102 with the opening 108. When a vacuum is applied to the skin 250 from within the housing 102, a portion of the skin 250 is pulled through the opening 108 and assumes a curved shape.

Figure 19B:
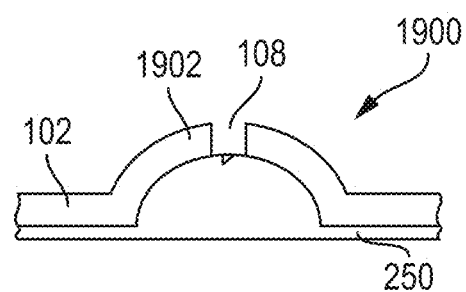

FIG. 19B illustrates a skin interface 1900 including a curved housing portion 1902. The curved housing portion 1902 can be located at least partially around the opening 108 in the housing 102. When a vacuum is applied to the skin 250 from within the housing 102, the skin 250 is pulled toward the opening 108 and against the bottom surface of the curved housing portion 1902, thus assuming a curvature similar to the curvature of the curved housing portion 1902.

Figure 19C:
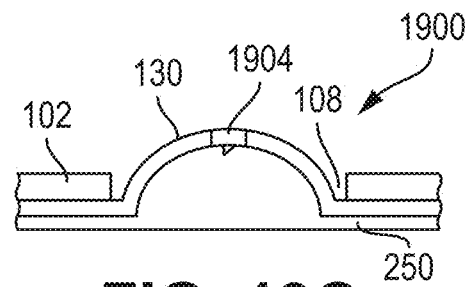

FIG. 19C illustrates a skin interface 1900 including a relatively thin flexible membrane 130. In some embodiments, the membrane 130 has a thickness less than or equal to about 250 µm, or within a range from about 50 µm to about 400 µm. The flexible membrane 130 is coupled to the housing 102 in a position at least partially covering the opening 108. The membrane 130 optionally includes an aperture 1904 to allow the skin-piercing feature (not shown) to pass through. When the bodily fluid collection device is applied to the patient's body, the membrane 130 contacts and couples to the skin 250 to provide an airtight seal against the skin 250. An adhesive may be applied to the bottom surface of the membrane 130 to facilitate sealing against the skin 250. When the membrane 130 is exposed to a vacuum from within the housing 102, the membrane 130 is pulled at least partially into the interior of the housing 102 and assumes a curved shape. Due to the seal between the skin 250 and the membrane 130, the skin 250 is also pulled toward the opening 108 and assumes a curvature similar to the curvature of the membrane 130.

Figure 19D:
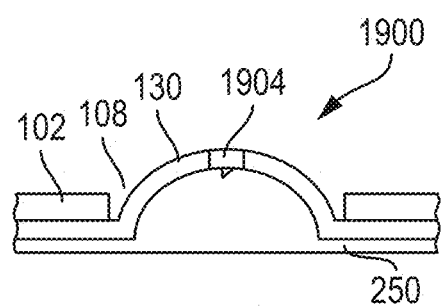

FIG. 19D illustrates a skin interface 1900 including a relatively thick flexible membrane 130. The skin interface 1900 is similar to the interface of FIG. 19C except that the flexible membrane 130 has an increased thickness. In some embodiments, the membrane 130 has a thickness greater than or equal to about 400 mm, or within a range from about 400 mm to about 800 mm. In some embodiments, a thinner membrane exhibits a higher curvature when exposed to vacuum and produces a higher skin curvature, while a thicker membrane exhibits a lower curvature when exposed to vacuum and produces a lower skin curvature. A higher skin curvature can be advantageous for maintaining the incision in an opened configuration, while a lower skin curvature can be advantageous for reducing bruising or other injuries to the surrounding portions of the skin 250.

Figure 19E:
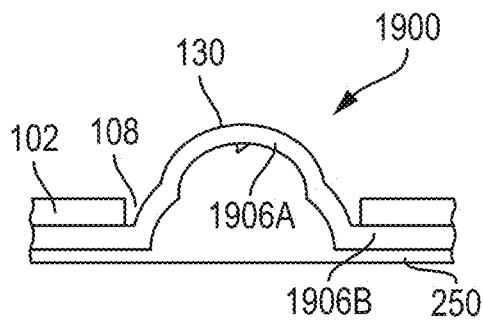

FIG. 19E illustrates a skin interface 1900 including a flexible membrane 130 with variable thickness. The skin interface 1900 is similar to the interfaces of FIG. 19C-19D, except that the flexible membrane 130 has a variable thickness. In the depicted embodiment, the membrane 130 has a central portion 1906A and an outer portion 1906B. The central portion 1906A can be thinner and have a higher curvature when exposed to vacuum, while the outer portion 1906B can be thicker and have a lower curvature when exposed to vacuum. For example, the central portion 1906A can have a thickness less than or equal to about 300 µm, or within a range from about 50 mm to about 300 µm; and the outer portion 1906B can have a thickness greater than or equal to about 300 µm, or within a range from about 300 µm to about 600 µm. Accordingly, the portion of the skin 250 near the central portion 1906A can have a higher curvature than the portion of the skin 250 near the outer portion 1906B. This configuration can be advantageous for maintaining the incision in an open position while reducing injuries to other portions of the skin 250. Alternatively, the thicknesses of the central portion 1906A and outer portion 1906B can be reversed, such that the central portion 1906A is thicker than the outer portion 1906B.

In some embodiments, the flexible membrane provides more precise control of the curvature of the skin than is achievable using vacuum pressure alone, even over relatively large skin surface areas. Accordingly, a bodily fluid collection device utilizing a flexible membrane as a skin interface can have a larger opening in the housing to allow for bodily fluid to be withdrawn from a greater skin surface area, thus increasing the potential draw volume. For example, the diameter of the opening can be at least about 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm. In some embodiments, the diameter is within a range from about 9 mm to about 27 mm.

Figure 20:
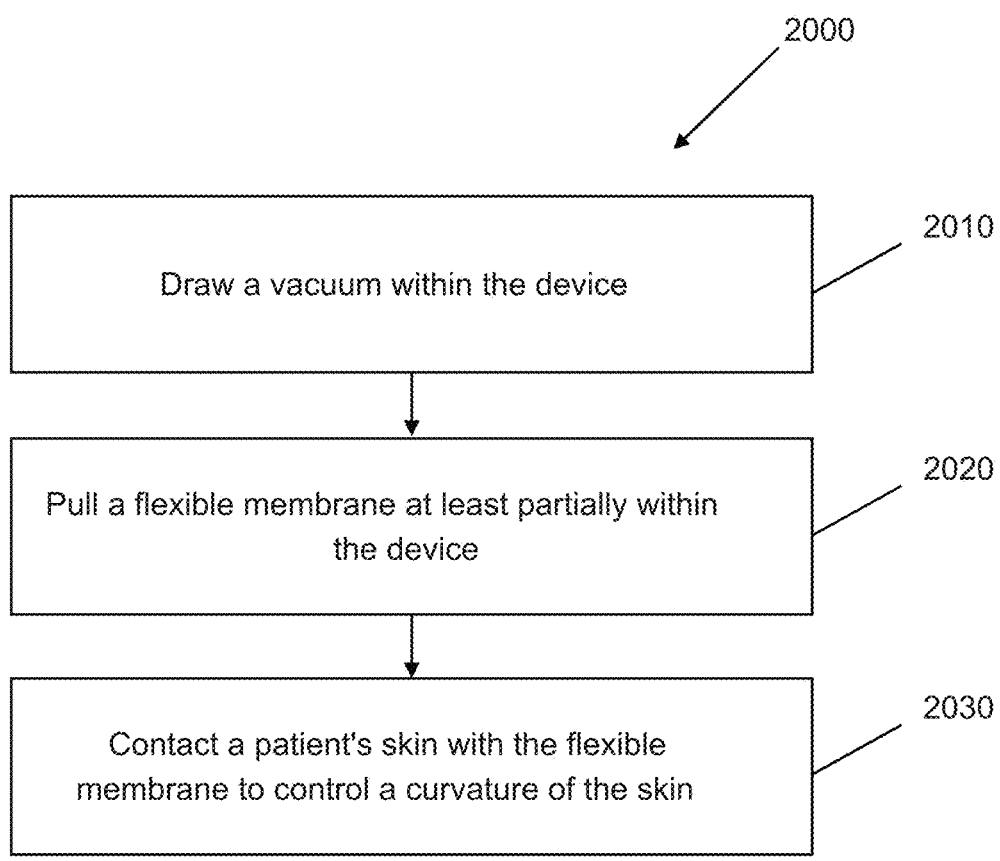
FIG. 20 is a block diagram of a method for withdrawing bodily fluid from a patient's skin using a flexible membrane in accordance with an embodiment of the present technology.

FIG. 20 is a block diagram of a method 2000 for withdrawing bodily fluid from a patient's skin using a flexible membrane configured in accordance with an embodiment the present technology. The method 2000 can be applied to any embodiment of the bodily fluid collection devices disclosed herein, such as the device 100. Additionally, one or more steps of the method 2000 can be combined with or substituted for any of the steps of the other methods disclosed herein. For example, one or more steps of the method 2000 can be performed in combination with or as sub-steps of block 340 and/or block 350 of the method 300.

The method 2000 includes drawing a vacuum within the device (block 2010). The vacuum can be generating using any of the vacuum mechanisms disclosed herein, such as the vacuum mechanisms described with reference to FIGS. 13A-18B. The method 2000 further includes pulling a flexible membrane at least partially within the device (block 2020). For example, the flexible membrane can be coupled to the bottom surface of the housing in a position covering at least a portion of the opening, and the flexible membrane can be pulled at least partially through the opening when exposed to the vacuum.

The method further includes contacting a patient's skin with the flexible membrane to control a curvature of the skin (block 2030). In some embodiments, the patient's skin is also pulled at least partially through the opening and into the device. The flexible membrane can assume a curved shape when exposed to the vacuum, and the patient's skin can be sealed against the flexible membrane so as to assume a similar curved shape.

Figure 21A:
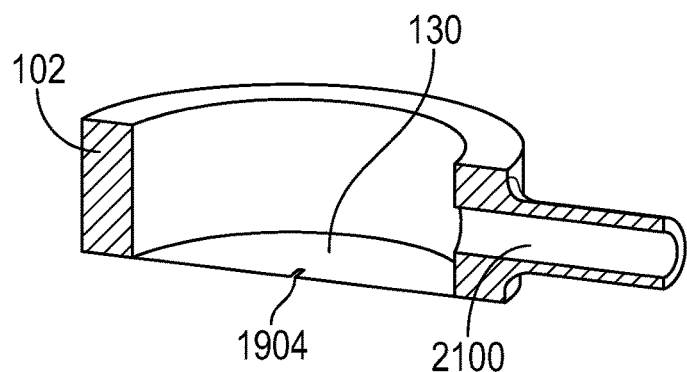
FIGS. 21A-21C are cross-sectional and perspective views of the flexible membrane of a bodily fluid collection device in accordance with an embodiment of the present technology.
Figure 21C:
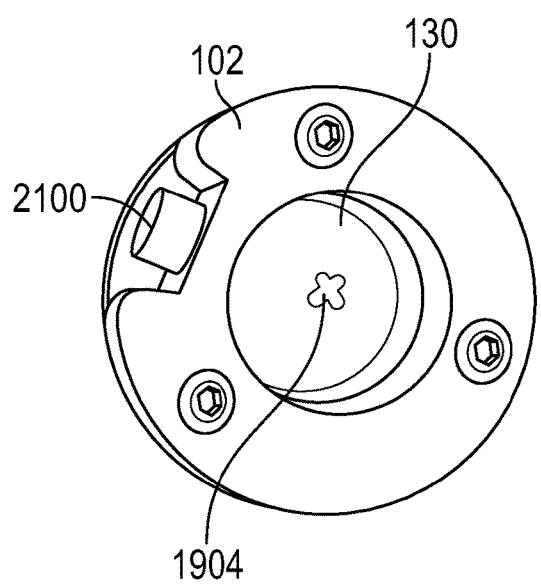
Figure 21B:
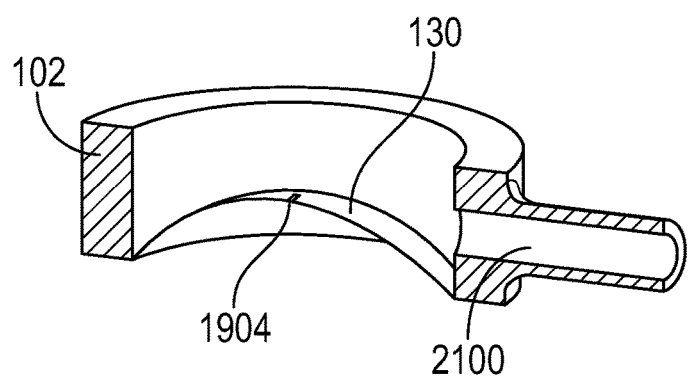

FIGS. 21A-21C are cross-sectional and perspective views of the flexible membrane 130 of a bodily fluid collection device configured in accordance with an embodiment the present technology. The device includes the opening 108 formed in the housing 102, and the membrane 130 is coupled to the housing 102 and covers at least a portion of the opening 108. Optionally, the membrane 130 can include an aperture 1904 to allow the skin-piercing feature of the device to pass through the membrane 130 during deployment. Alternatively, the membrane 130 may be provided without any aperture, and the skin-piercing feature can puncture the membrane 130 during deployment to form the aperture 1904. Prior to being exposed to a vacuum (FIG. 21A), the membrane 130 is in a generally planar configuration, with little or no curvature. When a vacuum is drawn within the housing 102 of the device (FIG. 21B), the membrane 130 is pulled at least partially within the housing 102 and into a curved shape. Bodily fluid is withdrawn into the housing 102 via the aperture 1904, and can be directed into a collection reservoir (not shown) via a channel 2100.

Figure 22:
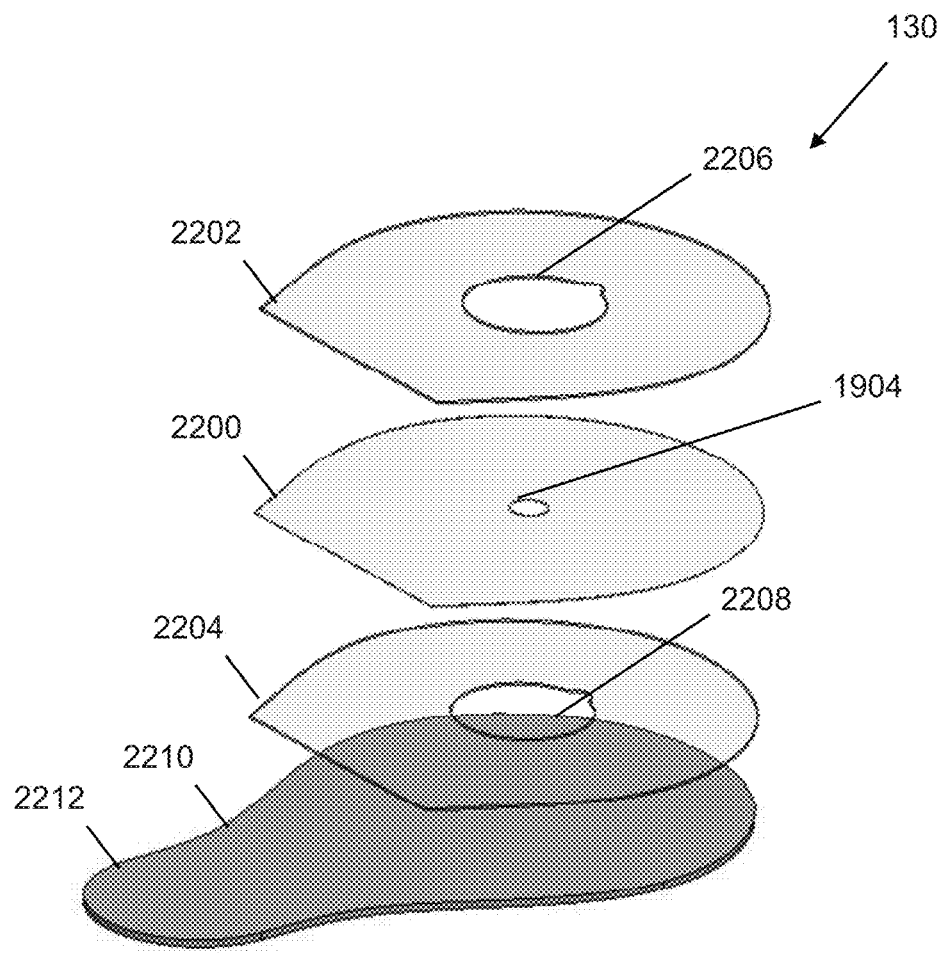
FIG. 22 is an exploded view of the flexible membrane configured in accordance with an embodiment of the present technology.

FIG. 22 is an exploded view of the flexible membrane 130 configured in accordance with an embodiment the present technology. The membrane 130 includes a film 2200, a first adhesive layer 2202, and a second adhesive layer 2204. The film 2200 can be a thin film of a flexible material, such as polyurethane or silicone. The first adhesive layer 2202 can be a double-sided adhesive that adheres to both the film 2200 and the housing of the bodily fluid collection device. The second adhesive layer 2204 can be a double-sided adhesive that adheres to both the film 2200 and a portion of the patient's skin. The adhesive material of the first and second adhesive layers 2202, 2204 can be selected such that when the device is applied to the patient's body, the flexible membrane 130 forms an airtight seal between the housing and the patient's skin. In alternative embodiments, the first adhesive layer 2202, second adhesive layer 2204, or both may be omitted from the membrane 130.

The film 2200 can include an aperture 1904 for the skin-piercing feature to pass through during deployment. The first adhesive layer 2202 can include an aperture 2206 formed within a central portion of the first adhesive layer 2202. The second adhesive layer 2204 can include an aperture 2208 formed within a central portion of the second adhesive layer 2204. The apertures 2206, 2208 can have a size and/or shape similar to the size and/or shape of the opening in the housing.

The membrane 130 can be provided with a liner 2210 that protects the membrane 130 prior to use, e.g., during storage and/or transportation. The liner 2406 can be removed to expose the second adhesive layer 2204 so that the flexible membrane 130 can be applied to and sealed against the patient's skin. Optionally, the liner 2210 can include a tab portion 2212 that extends beyond the housing of the device (e.g., as shown in FIG. 6A) to facilitate removal of the liner 2210.

In some embodiments, the membrane can be directly cast into the base of the bodily fluid collection device itself using thermoplastic elastomeric materials or silicone materials. This manufacturing method would remove the need for the first adhesive layer 2202 and as these manufacturing methods do not require the membrane to be planar, they would enable the creation of structural or functional features on the membrane itself.

In some embodiments, the flexible membranes of the present technology include one or more surface features and/or treatments to enhance flow of the bodily fluid from the patient's skin and into the device. For the example, the surface features and/or treatments can be configured to reduce coagulation of the bodily fluid (e.g., blood coagulation), reduce adhesion of the bodily fluid to the patient's skin, reduce adhesion of the bodily fluid to the membrane, direct flow of the bodily fluid toward a desired location (e.g., toward the collection reservoir), and/or direct flow of the bodily fluid away from an undesired location. The surface features and/or treatments can be on a lower surface of the membrane (e.g., the surface toward the patient's skin), the upper surface of the membrane (e.g., the surface away from the patient's skin), or both. The upper and lower surfaces of the membrane can have the same features and/or treatments, or can have different features and/or treatments.

Figure 23A:
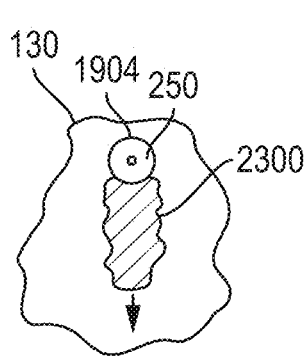
FIGS. 23A-23E are various views of flexible membranes with different surface features and/or treatments configured in accordance with embodiments of the present technology.

FIGS. 23A-23E are various views of portions of flexible membranes with different surface features and/or treatments configured in accordance with an embodiment the present technology. For example, FIG. 23A is a schematic illustration of a top view of the flexible membrane 130 without surface features and/or treatments. The membrane 130 includes an aperture 1904 (e.g., pre-formed in the membrane 130 or formed by the skin-piercing feature) through which bodily fluid 2300 is withdrawn from the patient's skin 250. The fluid 2300 may spread and smear across the skin 250 and/or membrane 130, thus making it more difficult to collect the fluid 2300.

Figure 23B:
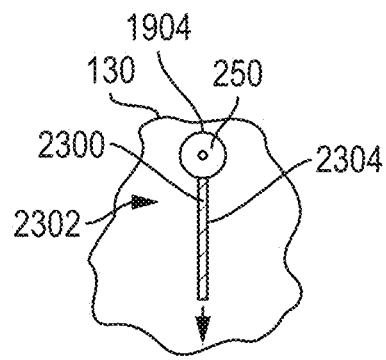

FIG. 23B is a schematic illustration of a top view of the flexible membrane 130 with micropatterned features 2302. The micropatterned features 2302 can include various combinations of channels, ridges, grooves, surface modifications, or patterned surface treatments or coatings, and the like. The micropatterned features 2302 can be shaped and positioned to direct flow of the bodily fluid toward a desired location, such as toward the collection reservoir. For example, in the embodiment of FIG. 23B, the micropatterned features 2302 include a linear channel 2304 extending from the aperture 1904 toward the reservoir. Bodily fluid 2300 withdrawn from the skin 250 can flow into the channel 2304 and toward the reservoir. In some embodiments where multiple incisions are made on the same membrane these features can be used to combine the bodily fluids from multiple incisions or alternatively to keep them separate and allow different treatments to be made to the flowing fluids. Furthermore, this approach can allow the direction of the multiple flows of bodily fluids toward different or separate reservoirs or containers.

Figure 23D:
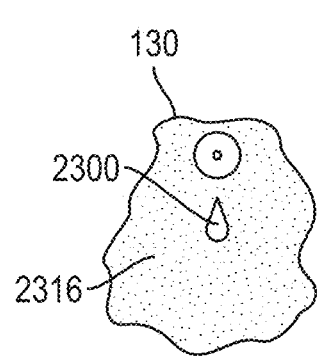
Figure 23C:
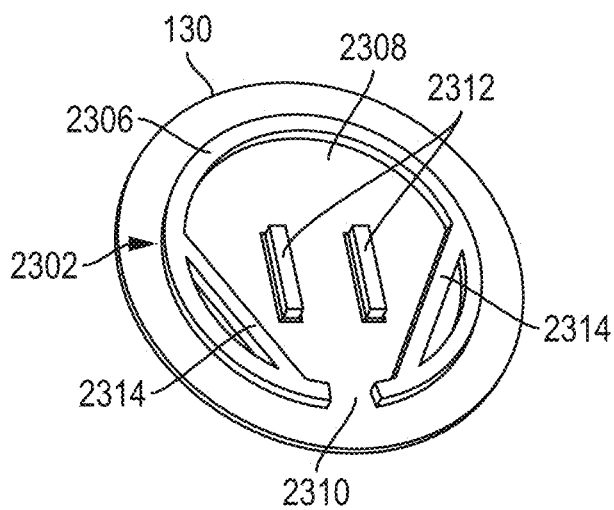

FIG. 23C is a perspective top view of a portion of the flexible membrane 130 with micropatterned features 2302. The features 2302 include a circular ridge 2306 defining a chamber 2308 that contains the bodily fluid. The ridge 2306 can define an opening 2310 in the chamber 2308 that is oriented toward the collection reservoir to direct the bodily fluid into the reservoir. The features 2302 can also include ridges, parallel ridges 2312, or multiple ridges within the chamber 2308. The ridges 2312 can be on either side of the location where the skin-piercing feature punctures the membrane 130 to direct bodily fluid toward the opening 2310, or along the path of the flow to act as a capillary guidance to the flow of fluids. The features 2302 can also include a pair of angled ridges 2314 within the chamber 2308 near the opening 2310. The angled ridges 2314 can serve to funnel bodily fluid from within the chamber 2308 toward the opening 2310.

FIG. 23D is a schematic illustration of a top view of a portion of the flexible membrane 130 with a hydrophobic coating 2316 (e.g., a silicone coating). The hydrophobic coating 2316 can be applied to the membrane 130 (e.g., by spray-coating). Alternatively, the membrane 130 itself can be made of a hydrophobic material. When the bodily fluid 2300 contacts the coating 2316, it forms into droplets that move easily across the surface of the membrane 130 with little or no sticking.

Figure 23E:
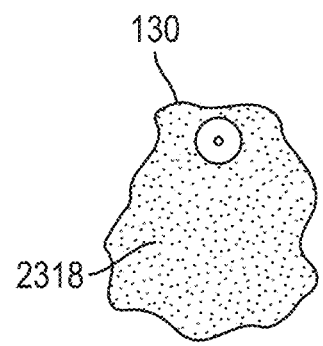

FIG. 23E is a schematic illustration of a top view of a portion of the flexible membrane 130 with an anticoagulant coating 2318. In some embodiments, the anticoagulant coating 2318 includes spray-coated EDTA. The anticoagulant coating 2318 can reduce the coagulation of the bodily fluid, thus improving flow into the reservoir.

FIGS. 24A-24F are cross-sectional views of housing features to control flow of bodily fluid along a flexible membrane 130 configured in accordance with an embodiment the present technology. In some embodiments, accumulation of bodily fluid 2300 at the outer portion 1906B of the flexible membrane 130 is undesirable. Such accumulation may occur if the angle between the outer portion 1906B and the portion of the housing 102 adjacent to the outer portion 1906B ("base portion 2400") is sufficiently small, e.g., less than about 90 degrees. For example, although the angle between the outer portion 1906B and the base portion 2400 may initially be greater than or equal to about 90 degrees (FIG. 24A), the angle may decrease to less than 90 degrees when the membrane 130 is curved (FIG. 24B). The decreased angle may pull bodily fluid between the outer portion 1906B and the base portion 2400, e.g., via capillary action.

FIGS. 24C and 24D illustrate a shelf 2402 to reduce flow of bodily fluid between the outer portion 1906B and the base portion 2400. The shelf 2402 can be formed in the base portion 2400 and can extend radially inward to partially cover the opening 108. When the membrane 130 is curved (FIG. 24D), bodily fluid 2300 can flow onto the shelf 2402, rather than becoming trapped between the base portion 2400 and the membrane 130.

FIGS. 24E and 24F illustrate an angled base portion 2400 to reduce flow of bodily fluid between the outer portion 1906B and the base portion 2400. The geometry of the angled based portion 2400 can be configured such that when the membrane 130 is curved (FIG. 24F), the angle between the base portion 2400 and the outer portion 1906B of the membrane 130 is sufficiently large to avoid drawing bodily fluid 2300 between the outer portion 1906B and the base portion 2400.

FIGS. 25A-25F are cross-sectional and top views of a wicking element 2500 for directing flow of a bodily fluid 2300 configured in accordance with an embodiment the present technology. The wicking element 2500 can be used in combination with or as an alternative to the flexible membranes disclosed herein. The wicking element 2500 can be made of an absorbent material, and can optionally include an anticoagulant. The wicking element 2500 can include a first wicking portion 2502A and a second wicking portion 2502B. The first wicking portion 2502A can be shaped to at least partially cover the opening 108 of the housing 102, and can optionally include an aperture for the skin-piercing feature 116 to pass through. The second wicking portion 2502B can have an elongated shape configured to direct bodily fluid 2300 into the housing 102 toward the collection reservoir.

Figure 25A:
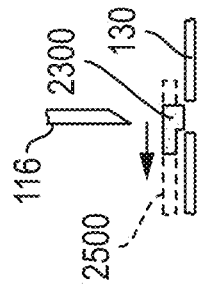
FIGS. 25A-25F are cross-sectional and top views of a wicking element for directing flow of a bodily fluid in accordance with an embodiment of the present technology.
Figure 25C:
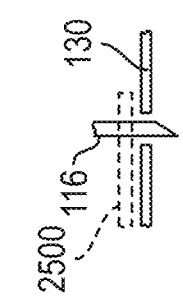
Figure 25E:
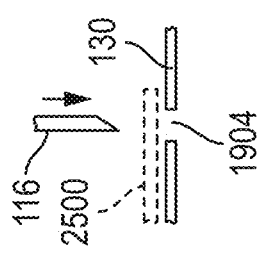
Figure 25B:
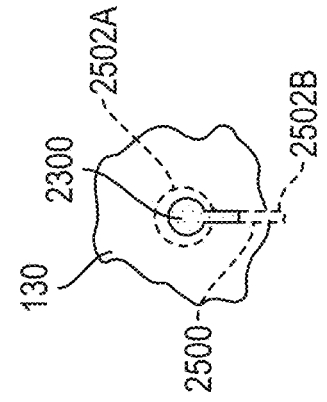
Figure 25D:
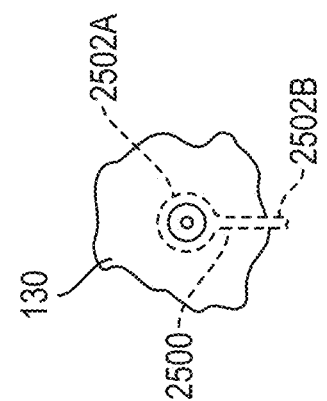
Figure 25F:
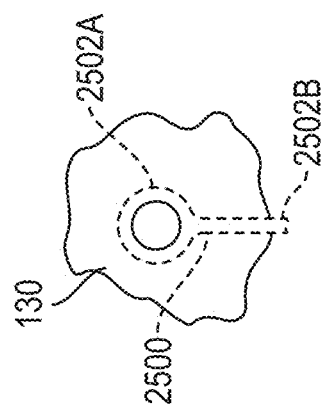

In some embodiments, the wicking element 2500 is positioned over the flexible membrane 130, with the first wicking portion 2502A over the aperture 1904 in the membrane 130, and the second wicking portion 2502B extending along the membrane 130 toward the interior of the housing (FIGS. 25A (cross-sectional view) and 25B (top view)). The skin-piercing feature 116 can be deployed through the first wicking portion 2502A to pierce the patient's skin (FIGS. 25C (cross-sectional view) and 25D (top view)). The skin-piercing feature 116 can subsequently be retracted through the first wicking portion 2502A to permit withdrawal of bodily fluid 2300 (FIGS. 25E (cross-sectional view) and 25F (top view)). A first portion of the bodily fluid 2300 can be absorbed into the wicking element 2500. Once the wicking element 2500 is saturated, a remaining portion of the bodily fluid 2300 can flow between the second wicking portion 2502B and the flexible membrane 130 toward the collection reservoir. In some embodiments, the first portion of the bodily fluid 2300 includes contaminants or is otherwise undesirable for testing and analysis of the bodily fluid 2300. Accordingly, the wicking element 2500 can be used to absorb and discard the first portion of the bodily fluid 2300, while directing the remaining portion of the bodily fluid 2300 into the housing and reservoir for collection. Furthermore, the wicking element can be utilized to guide the flow of fluids over the membrane or plastic and deliver chemical treatments to the fluid rapidly after it is extracted from the skin.

V. CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

From the foregoing, it will be appreciated that specific embodiments of the present technology have been described herein for purposes of illustration, but that various modifications may be made without deviating from the scope of the present technology. Accordingly, the present technology is not limited except as by the appended claims.

We claim:

1. A device for withdrawing bodily fluid from a subject, the device comprising:
   a housing defining a lumen and including a base and an outflow channel, wherein the base includes an upper surface, a lower surface, and an opening extending between the upper and lower surfaces, wherein the housing is configured to receive the bodily fluid in the lumen through the opening in the base, and wherein the outflow channel is configured to be releasably coupled to a collection reservoir;
   a flexible membrane at least partially on the lower surface of the base, wherein the flexible membrane has an upper surface facing the lumen and a lower surface configured to be positioned against skin of the subject to provide a seal between the skin and the base around the opening, and wherein the upper surface of the base is configured to direct the bodily fluid laterally thereacross from the opening at least partially to the outflow channel;
   a skin-piercing assembly including a skin-piercing feature and a first biasing member, wherein the first biasing member is fixed to the skin-piercing feature to bias the skin-piercing feature toward the opening in a deployment direction;
   an actuator movable relative to the housing in the deployment direction,
      wherein movement of the actuator in the deployment direction to a loading position increases a load on the first biasing member, and
      wherein movement of the actuator in the deployment direction beyond the loading position releases the load on the first biasing member such that the first biasing member drives the skin-piercing feature in the deployment direction;
   a second biasing member coupled to the skin-piercing assembly, wherein the second biasing member is configured to drive the skin-piercing assembly in a retraction direction after the first biasing member drives the skin-piercing feature in the deployment direction; and
   a flexible member extending over the opening in the base to define a sealed region over the base,
      wherein movement of the actuator in the deployment direction compresses the flexible member to decrease a volume of the sealed region, and
      wherein, after the first biasing member drives the skin-piercing feature in the deployment direction, the flexible member is configured to at least partially decompress to increase the volume of the sealed region to generate vacuum pressure in the sealed region.

2. The device of claim 1 wherein movement of the actuator in the retraction direction permits the flexible member to at least partially decompress.

3. The device of claim 1, further comprising a one-way valve in fluid communication with the sealed region, wherein the one-way valve is configured to (a) permit air to move out of the sealed region when the flexible member compresses and (b) inhibit air from moving into the sealed region when the flexible member decompresses.

4. The device of claim 3 wherein the valve is an umbrella valve.

5. The device of claim 1 wherein the skin-piercing assembly is positioned within the sealed region.

6. The device of claim 1 wherein the first biasing member is a coil spring.

7. The device of claim 1, further comprising a tube connector in fluid communication with the sealed region, wherein a collection tube is configured to be releasably secured to the tube connector.

8. The device of claim 7, further comprising the collection tube.

9. The device of claim 1 wherein the skin-piercing feature includes a needle.

10. The device of claim 1 wherein the load on the first biasing member is non-zero before movement of the actuator in the deployment direction.

11. The device of claim 1 wherein the flexible membrane includes an adhesive.

12. The device of claim 1 wherein the flexible membrane is configured to be drawn at least partially through the opening in the base when the vacuum pressure is generated in the sealed region.

13. A device for withdrawing blood from a subject, the device comprising:
- a housing defining a lumen and including a base and an outflow channel, wherein the base includes an upper surface, a lower surface, and an opening extending between the upper and lower surfaces, wherein the lower surface is configured to be positioned proximate skin of the subject, wherein the housing is configured to receive the blood in the lumen through the opening in the base, and wherein the outflow channel is configured to be releasably coupled to a collection reservoir;
- a flexible membrane at least partially on the lower surface of the base, wherein the flexible membrane has an upper surface facing the lumen and a lower surface configured to be positioned against the skin of the subject to provide a seal between the skin and the base around the opening, and wherein the upper surface of the flexible membrane is configured to direct the bodily fluid laterally thereacross from the opening at least partially to the outflow channel;
- a skin-piercing assembly including a skin-piercing feature;
- a biasing member fixed to the skin-piercing feature;
- an actuator operably coupled to the skin-piercing assembly via the biasing member,
    - wherein the actuator is movable relative to the housing in a deployment direction and a retraction direction,
    - wherein movement of the actuator in the deployment direction to a loading position increases a load on the biasing member, and
    - wherein movement of the actuator in the deployment direction beyond the loading position releases the load on the biasing member such that the biasing member drives the skin-piercing feature in the deployment direction through the opening in the base and into the skin of the subject to form an incision in the skin of the subject;
- a flexible member extending over the opening in the base to define a sealed region over the base,
    - wherein movement of the actuator in the deployment direction compresses the flexible member to decrease a volume of the sealed region, and
    - wherein, after the biasing member drives the skin-piercing feature in the deployment direction, the flexible member is configured to at least partially decompress to increase the volume of the sealed region to generate vacuum pressure in the sealed region to draw blood from the incision into the sealed region;
- a tube connector in fluid communication with the sealed region; and
- a collection tube configured to be releasably secured to the tube connector for receiving the blood from the sealed region.

14. The device of claim 13 wherein the load on the biasing member is non-zero before movement of the actuator in the deployment direction.

15. The device of claim 13 wherein the deployment direction is a direction toward the skin of the subject.

16. The device of claim 13 wherein the actuator is configured to be pressed in the deployment direction by the subject.

17. The device of claim 13 wherein the biasing member is a coil spring.

18. The device of claim 13 wherein the biasing member is a first biasing member, and further comprising a second biasing member coupled to the skin-piercing assembly, wherein the second biasing member is configured to drive the skin-piercing assembly in the retraction direction after the first biasing member drives the skin-piercing feature in the deployment direction.

19. The device of claim 13 wherein the skin-piercing assembly is positioned in the sealed region.

20. The device of claim 13 wherein the flexible member extends over the skin-piercing assembly.

21. The device of claim 13, further comprising a one-way valve in fluid communication with the sealed region, wherein the one-way valve is configured to (a) permit air to move out of the sealed region when the flexible member compresses and (b) inhibit air from moving into the sealed region when the flexible member decompresses.

22. The device of claim 13 wherein the skin-piercing feature includes a plurality of needles.

* * * * *